United States Patent [19]

Hur et al.

[11] Patent Number: 5,521,146
[45] Date of Patent: May 28, 1996

[54] HERBICIDAL PYRIMIDINE DERIVATIVES, PROCESS FOR PREPARATION THEREOF AND THEIR USE AS HERBICIDE

[75] Inventors: Chang U. Hur; Jin H. Cho; Su M. Hong; Hong W. Kim; Young H. Lim; Jae S. Rim; Jeong S. Kim; Sang H. Chae, all of Daejeon, Rep. of Korea

[73] Assignee: Lucky Ltd., Rep. of Korea

[21] Appl. No.: 339,249

[22] Filed: Nov. 10, 1994

[30] Foreign Application Priority Data

Nov. 13, 1993 [KR] Rep. of Korea ............... 1993-24099
Dec. 27, 1993 [KR] Rep. of Korea ............... 1993-30055
Dec. 29, 1993 [KR] Rep. of Korea ............... 1993-31016

[51] Int. Cl.$^6$ ............... C07D 239/60; C07D 403/12; C07D 409/12; A01N 43/54

[52] U.S. Cl. ............... 504/243; 544/296; 544/300; 544/301

[58] Field of Search ............... 544/300, 301, 544/296; 504/243

[56] References Cited

PUBLICATIONS

Wada et al, Chemical Abstracts, vol. 119, entry 100312 (1993).
Wada et al, Chemical Abstracts vol. 111, entry 93933 (1989).

*Primary Examiner*—John M. Ford
*Attorney, Agent, or Firm*—Birch, Stewart, Kolasch & Birch

[57] ABSTRACT

The invention relates to novel herbicidal compounds and compositions. The compounds of the invention are highly substituted derivatives of pyrimidine.

13 Claims, No Drawings

HERBICIDAL PYRIMIDINE DERIVATIVES, PROCESS FOR PREPARATION THEREOF AND THEIR USE AS HERBICIDE

BACKGROUND OF THE INVENTION

1. Field of the Invention

The present invention relates to a novel herbicidal pyrimidine derivative. More particularly, the present invention relates to a novel herbicidal 2-(4,6-dimethoxypyrimidin-2-yl)oxybenzoic acid imino ester derivative represented by the following general formula (I):

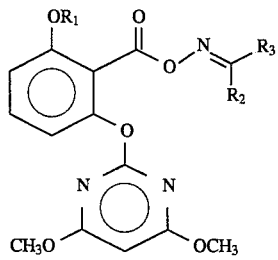

in which

R$_1$ represents 4,6-dimethoxy-2-pyrimidinyl, C$_1$–C$_4$ alkyl, C$_2$–C$_4$ alkenyl, acyl, C$_1$–C$_4$ alkyl sulfonyl or heteroarylmethyl;

R$_2$ represents hydrogen, halogen, cyano, nitro, C$_1$–C$_8$ alkyl, C$_1$–C$_8$ alkoxy, C$_1$–C$_8$ alkylthio, C$_1$–C$_8$ alkoxycarbonyl, C$_2$–C$_4$ alkenyloxycarbonyl, arylmethoxycarbonyl, heteroarylmethoxycarbonyl, C$_1$–C$_4$ alkylaminocarbonyl, aryl-C$_1$–C$_4$ alkylaminocarbonyl, heteroarylmethylaminocarbonyl, aryl, C$_2$–C$_8$ alkenyl, C$_3$–C$_6$ cycloalkyl, benzyl, aryloxy, arylthio or C$_1$–C$_8$ alkylcarbonyl; and R$_3$ represents phenyl group which can be optionally substituted with substituent selected from the group consisting of halogen, cyano, nitro, C$_1$–C$_4$ alkyl, C$_3$–C$_6$ cycloalkyl, C$_1$–C$_4$ alkoxy, C$_1$–C$_4$ alkenyloxy, C$_1$–C$_4$ alkylthio, amino which can be substituted with C$_1$–C$_4$ alkyl, aryl, aryloxy, C$_1$–C$_4$ acyl, C$_1$–C$_4$ acyloxy and C$_2$–C$_4$ alkenyl, or represents a group of formula —COR$_4$ wherein R$_4$ represents hydrogen, C$_1$–C$_4$ alkyl, C$_2$–C$_4$ alkenyl, C$_3$–C$_6$ cycloalkyl, benzyl, aryl, C$_1$–C$_4$ alkoxy, C$_2$–C$_4$ alkenyloxy, C$_3$–C$_6$ cycloalkyloxy, benzyloxy, aryloxy, C$_1$–C$_4$ alkylthio, C$_2$–C$_4$ alkenylthio, C$_3$–C$_6$ cycloalkylthio, benzylthio, arylthio, amino which can be substituted with C$_1$–C$_4$ alkyl, amino which can be substituted with aryl, or amino which can be substituted with arylmethyl.

The present invention also relates to a process for preparation of the compound of formula (I), as defined above, and to a herbicidal composition containing the compound of formula (I) as an active ingredient.

2. Background Art

In the prior art, it has been well known that 2-phenoxypyrimidine or (pyrimidin-2-yl)oxybenzene derivatives are useful as a herbicide (see Agr. Biol. Chem., Vol. 30, P.896 (1966); Japanese Laid-open Patent Publication No. 79-55729; U.S. Pat. Nos. 4,248,619 and 4,427,437). Recently, it has also been noted that among numerous compounds developed on the basis of 2-phenoxypyrimidine a 2-(pyrimidin-2-yl)oxybenzoic acid derivative has an excellent herbicidal activity (see European Patent Publication Nos. 223,406, 249,708, 287,072, 287,079, 315,889, 321,846, 330,990, 335,409, 346,789, 363,040, 402,751, 435, 170, 435,186, 457,505, 459,243 and 468,690, British Patent Publication No. 2,237,570 and German Patent Publication No. 3942476). Those prior known compounds show a mechanism of action similar to that of sulfonylurea derivatives, imidazolinol derivatives and triazolepyrimidine derivatives which have been known as an inhibitor of amino acid biosynthesis, and also have a merit of being easily prepared with their simple structures.

Herbicidal activity and selectivity on useful crops of those known compounds are varied with the kind of substituents on the benzene ring of 2-(pyrimidin-2-yl)oxybenzoic acid or with the type of benzoic acid ester derivatives. Accordingly, the development of novel herbicides has placed the focus on the introduction of different substituents into the benzene ring of 2-(pyrimidin- 2-yl)oxybenzoic acid and/or the formation of novel ester derivatives.

Thus, the present inventors have extensively studied to develop a novel ester derivative based on 2-(pyrimidin-2-yl)oxybenzoic acid, which shows a high herbicidal activity and selectivity on weeds but has no phytotoxicity on useful crops. According to this, we have identified that a certain imino ester compound having an aromatic ring or carbonyl moiety such as the compound of formula (I), as defined above, can exhibit an excellent herbicidal activity in comparison to the prior herbicidal ester derivatives, and then completed the present invention.

In addition, 2,6-di(pyrimidin-2-yl)oxybenzoic acid derivatives having an alkylimino ester structure which is similar to that of the compound of formula (I) according to the present invention have also been described in the prior art (see European Patent Publication No. 321,846). However, iminoester derivatives having an aromatic ring or carbonal moiety which is the same as that of the compound of formula (I) according to the present invention have never been disclosed and further, cannot be synthesized by the methods for preparing alkyliminio ester derivatives as disclosed in the said European Publication, even though, in some particular cases, they can be synthesized only with an extremely low yield (less than 5%). Accordingly, the present inventors have also developed, as well as an imino ester derivative (I) having an aromatic ring, a novel method for preparation thereof.

Thus, it is an object of the present invention to provide a novel herbicidal 2-(4,6-dimethoxypyrimidin-2-yl)oxybenzoic acid imino ester derivative having the general formula (I), as defined above.

It is another object of the present invention to provide a process for preparing the novel 2-(4,6-dimethoxypyrimidin-2-yl)oxybenzoic acid imino ester derivative of formula (I).

Further, it is still another object of the present invention to provide a herbicidal composition containing at least one of the novel 2-(4,6-dimethoxypyrimidin-2-yl)oxybenzoic acid imino ester derivative of formula (I) as an active ingredient.

It is further object of the present invention to provide a novel intermediate pyridine thio ester compound having the general formula (II) as defined below, which can be used as a starting material for preparing the compound of formula (I) of the present invention.

The foregoing has outlined some of the more pertinent objects of the present invention. These objects should be construed to be merely illustrative of some of the more pertinent features and applications of the invention. Other many beneficial results can be obtained by applying the disclosed invention in a different manner or modifying the invention within the scope of the disclosure. Accordingly, other objects and a more thorough understanding of the invention may be had by referring to the disclosure of invention, in addition to the scope of the invention defined by the claims.

DISCLOSURE OF INVENTION

In one aspect, the present invention relates to a novel 2-(4,6-dimethoxypyrimidin-2-yl)oxybenzoic acid imino ester derivative represented by the following general formula (I):

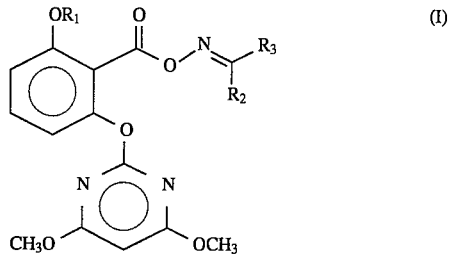

in which $R_1$ represents 4,6-dimethoxy-2-pyrimidinyl, $C_1$–$C_4$ alkyl, $C_2$–$C_4$ alkenyl, acyl, $C_1$–$C_4$ alkyl sulfonyl or heteroarylmethyl;

$R_2$ represents hydrogen, halogen, cyano, nitro, $C_1$–$C_8$ alkyl, $C_1$–$C_8$ alkoxy, $C_1$–$C_8$ alkylthio, $C_1$–$C_8$ alkoxycarbonyl, $C_2$–$C_4$ alkenyloxycarbonyl, arylmethoxycarbonyl, heteroarylmethoxycarbonyl, $C_1$–$C_4$ alkylaminocarbonyl, aryl-$C_1$–$C_4$ alkylaminocarbonyl, heteroarylmethylaminocarbonyl, aryl, $C_2$–$C_8$ alkenyl, $C_3$–$C_6$ cycloalkyl, benzyl, aryloxy, arylthio or $C_1$–$C_8$ alkylcarbonyl; and $R_3$ represents phenyl group which can be optionally substituted with substituent selected from the group consisting of halogen, cyano, nitro, $C_1$–$C_4$ alkyl, $C_3$–$C_6$ cycloalkyl, $C_1$–$C_4$ alkoxy, $C_2$–$C_4$ alkenyloxy, $C_1$–$C_4$ alkylthio, amino which can be substituted with $C_1$–$C_4$ alkyl, aryl, aryloxy, $C_1$–$C_4$ acyl, $C_1$–$C_4$ acyloxy and $C_2$–$C_4$ alkenyl, or represents a group of formula —$COR_4$ wherein $R_4$ represents hydrogen, $C_1$–$C_4$ alkyl, $C_2$–$C_4$ alkenyl, $C_3$–$C_6$ cycloalkyl, benzyl, aryl, $C_1$–$C_4$ alkoxy, $C_2$–$C_4$ alkenyloxy, $C_3$–$C_6$ cycloalkyloxy, benzyloxy, aryloxy, $C_1$–$C_4$ alkylthio, $C_2$–$C_4$ alkenylthio, $C_3$–$C_6$ cycloalkylthio, benzylthio, arylthio, amino which can be substituted with $C_1$–$C_4$ alkyl, amino which can be substituted with aryl, or amino which can be substituted with arylmethyl.

In the definitions for the substituents of the compound of formula (I), the term "alkyl" which is used alone or in the form of a composite term such as "alkylthio", "alkylsulfonyl" or "alkylaminocarbonyl" means a straight or branched, saturated hydrocarbon radical, for example, methyl, ethyl, n-propyl, iso-propyl, n-butyl or its isomers, etc.; the term "alkoxy" means a straight or branched alkoxy group, for example, methoxy, ethoxy, n-propoxy, isopropoxy, n-butoxy or its isomers, etc.; the term "alkenyl" which is used alone or in the form of a composite term such as "alkenyloxy" means a straight or branched alkene, for example, vinyl, 1-propenyl, 2-propenyl, various isomers of butenyl, pentenyl, hexenyl, heptenyl, etc. the term "aliphatic acyl" means acetyl, propionyl, etc.; and the term "halogen" means fluorine, chlorine, bromine, iodine, etc. In addition, the term "aryl" which is used alone or in the form of a composite term such as "aryloxy", "arylthio" or "aryl-$C_1$–$C_4$ alkylaminocarbonyl" defines a phenyl group which is unsubstituted or substituted with a substituent selected from the group consisting of alkyl, alkoxy and halogen. The term "heteroaryl" used in the composite term "heteroarylmethyl", "heteroarylmethylcarbonyl" or "heteroarylmethoxycarbonyl" defines a 5- to 6-membered ring containing at least one hetero atom selected from oxygen, sulfur and nitrogen as ring member for example, furyl, thienyl, pyridine, piperidine, etc.

One preferred group of the novel compound of formula (I) according to the present invention includes the compounds wherein $R_1$ represents 4,6-dimethoxy-2-pyrimidinyl;

$R_2$ represents hydrogen, halogen, cyanophenyl, $C_1$–$C_8$ alkyl, $C_1$–$C_4$ alkoxy, $C_1$–$C_4$ alkylthio, $C_1$–$C_4$ alkoxycarbonyl, mono- or di-$C_1$–$C_4$ alkylaminocarbonyl, phenyl-$C_1$–$C_2$ alkylaminocarbonyl wherein the phenyl moiety can be optionally substituted with halogen, $C_1$–$C_2$ alkyl or $C_1$–$C_2$ alkoxy, furylmethylaminocarbonyl or phenyl; and $R_3$ represents phenyl group which is unsubstituted or substituted with halogen, cyano, nitro, $C_1$–$C_4$ alkyl, $C_1$–$C_4$ alkoxy, allyloxy, $C_1$–$C_4$ alkylthio, amino which can be substituted with $C_1$–$C_4$ alkyl, phenoxy, benzyloxy or acetoxy, or represents a group of formula —$COR_4$ wherein $R_4$ represents $C_1$–$C_4$ alkoxy, $C_1$–$C_4$ alkyl, benzyloxy or benzylamino.

The most preferred compound of the said preferred group of the compound of formula (I) according to the present invention includes those wherein $R_1$ represents 4,6-dimethoxy-2-pyrimidinyl;

$R_2$ represents hydrogen, chloro, cyanophenyl, $C_1$–$C_8$ alkyl, methoxy, methylthio, $C_1$–$C_2$ alkoxycarbonyl, propylaminocarbonyl, dimethylaminocarbonyl, benzylaminocarbonyl wherein the benzyl moiety is optionally substituted with chloro, methyl or methoxy, 2'-phenylethylaminocarbonyl, furylmethylaminocarbonyl or phenyl; and $R_3$ represents phenyl group which is unsubstituted or substituted with a substituent selected from the group consisting of chloro, fluoro, cyano, nitro, methyl, methoxy, ethoxy, butoxy, allyloxy, methylthio, dimethylamino, phenoxy, benzyloxy or acetoxy, or represents a group of formula —$COR_4$ wherein $R_4$ represents methoxy, ethoxy, methyl, benzyloxy or benzylamino.

Another preferred group of the compound of formula (I) according to the present invention includes the compounds wherein $R_1$ represents $C_1$–$C_2$ alkyl, $C_2$–$C_4$ alkenyl, allyl, acetyl, methylsulfonyl, thienylmethyl or furylmethyl;

$R_2$ represents hydrogen, $C_1$–$C_4$ alkyl, $C_1$–$C_4$ alkoxy, $C_1$–$C_4$ alkylthio, cyano or $C_1$–$C_4$ alkoxycarbonyl; and $R_3$ represents phenyl group which is unsubstituted or substituted with $C_1$–$C_4$ alkyl, $C_1$–$C_4$ alkoxy or $C_2$–$C_4$ alkenyl.

The particularly preferred compound of the said preferred group of the compound of formula (I) according to the present invention includes those wherein $R_1$ represents methyl, ethyl, allyl, acetyl, methylsulfonyl, thienylmethyl or furylmethyl;

$R_2$ represents hydrogen, methyl, methylthio, cyano or methoxycarbonyl; and $R_3$ represents phenyl group which is unsubstituted or substituted with methyl or methoxy.

The compound of formula (I) according to the present invention, as defined above, exhibits an excellent herbicidal activity against all of gramineous weeds, broad leaf weeds, annual weeds and perennial weeds and has no phytotoxicity against useful crops such as cotton, wheat and rice plant at an herbicidally effective concentration thereof. Particularly, in the field of direct sowing rice plants the compound of the present invention can completely control troublesome annual and perennial weeds, including barnyardgrass, at an extremely low concentration and, at the same time, shows an excellent safety against the direct sowing rice plant. For example, the safety against direct sowing rice plant of the phenylimino ester compound according to the present invention is two times or more as high as that of 2,6-di(4,6-dimethoxypyrimidin-2-yl)oxybenzoic acid derivatives having an alkylimino ester structure as disclosed in European Patent Publication No. 321,846.

Typical examples of the compound of formula (I) according to the present invention are presented in the following Tables 1 to 3.

TABLE 1

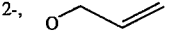

(I-A)

| Comp. No. | $R_5$ | | $R_2$ |
|---|---|---|---|
| 1 | | H | H |
| 2 | 2-, | Cl | H |
| 3 | 3-, | Cl | H |
| 4 | 4-, | Cl | H |
| 5 | 2-, | F | H |
| 6 | 4-, | F | H |
| 7 | 2-, | $CH_3$ | H |
| 8 | 3-, | $CH_3$ | H |
| 9 | 4-, | $CH_3$ | H |
| 10 | 2-, | $OCH_3$ | H |
| 11 | 3-, | $OCH_3$ | H |
| 12 | 4-, | $OCH_3$ | H |
| 13 | 2-, | $OC_2H_5$ | H |
| 14 | 4-, | $OC_2H_5$ | H |
| 15 | 2-, | OCH$_2$CH=CH$_2$ | H |
| 16 | 4-, | OBu | H |
| 17 | 4-, | OBn | H |
| 18 | 2-, | OPh | H |
| 19 | 3-, | OPh | H |
| 20 | 4-, | $SCH_3$ | H |
| 21 | 4-, | CN | H |
| 22 | 4-, | $NO_2$ | H |
| 23 | 4-, | OAc | H |
| 24 | | H | $CH_3$ |
| 25 | | H | $OCH_3$ |
| 26 | | H | $SCH_3$ |
| 27 | | H | Cl |
| 28 | | H | Ph |
| 29 | | H | CN |
| 30 | 4-, | $N(CH_3)_2$ | H |
| 31 | | H | $COOCH_3$ |
| 32 | 3-, | $CH_3$ | $COOC_2H_5$ |

TABLE 1-continued (I-A)

| Comp. No. | $R_5$ | | $R_2$ |
|---|---|---|---|
| 33 | | H | CON(Pr)(H) |
| 34 | | H | CON(CH$_3$)$_2$ |
| 35 | | H | CONHCH$_2$Ph |
| 36 | 4-, | Cl | CONHCH$_2$Ph |
| 37 | 4-, | $OCH_3$ | CONHCH$_2$Ph |
| 38 | 3-, | $OCH_3$ | CONHCH$_2$Ph |
| 39 | | H | CONHCH$_2$(C$_6$H$_4$-Cl) |
| 40 | | H | CONHCH$_2$(C$_6$H$_4$-CH$_3$) |
| 41 | | H | CONHCH$_2$(C$_6$H$_4$-OCH$_3$) |
| 42 | | H | CONHCH$_2$(C$_6$H$_4$-OCH$_3$) |

TABLE 1-continued (I-A)

| Comp. No. | $R_5$ | $R_2$ |
|---|---|---|
| 43 | H | CONH-CH2-furan |
| 44 | H | CONH-CH2CH2-phenyl |

TABLE 2

(I-B)

| Comp. No. | $R^4$ | $R^2$ |
|---|---|---|
| 45 | $OCH_3$ | H |
| 46 | $OC_2H_5$ | H |
| 47 | $CH_3$ | $CH_3$ |
| 48 | $OCH_3$ | $CH_3$ |
| 49 | O-CH2-phenyl | $CH_3$ |
| 50 | HN-CH2-phenyl | $CH_3$ |
| 51 | $OCH_3$ | $C_2H_5$ |
| 52 | $OC_2H_5$ | $i-C_3H_7$ |
| 53 | $OC_2H_5$ | $C_4H_9$ |
| 54 | O-CH2-phenyl | $C_4H_9$ |

TABLE 2-continued (I-B)

| Comp. No. | $R^4$ | $R^2$ |
|---|---|---|
| 55 | HN-CH2-phenyl | $C_4H_9$ |
| 56 | $OC_2H_5$ | $C_5H_{11}$ |
| 57 | $OC_2H_5$ | $C_8H_{17}$ |

TABLE 3

(I-C)

| Comp. No. | $R_1$ | $R_5$ | $R_2$ |
|---|---|---|---|
| 58 | $CH_3$ | 3'-, $CH_3$ | H |
| 59 | $CH_3$ | H | $CH_3$ |
| 60 | $CH_3$ | H | $SCH_3$ |
| 61 | $CH_3$ | 4'-, $C_2H_5$ | H |
| 62 | $C_2H_5$ | H | $CH_3$ |
| 63 | $C_2H_5$ | H | $SCH_3$ |
| 64 | $C2H_5$ | 4'-, $C_2H_5$ | H |
| 65 | $CH_2=CHCH_2$ | H | $CH_3$ |
| 66 | $CH_2=CHCH_2$ | H | $SCH_3$ |
| 67 | $CH_2=CHCH_2$ | H | H |
| 68 | $CH_2=CHCH_2$ | H | CN |
| 69 | $CH_2=CHCH_2$ | H | $CO_2CH_3$ |
| 70 | $COCH_3$ | H | H |
| 71 | $CH_3SO_2$ | H | H |
| 72 | thiophene-$CH_2$ | H | H |
| 73 | furan-$CH_2$ | H | H |

Since in the compounds having substituents on '2,6'-positions of benzoic acid as in the compound of formula (I) according to the present invention a carboxylic group is seriously sterically hindered, it is very difficult to prepare their imino ester derivatives in high yield by using conventional methods [see Tetrahedron, Vol. 36, P.2409 (1980), J. Org. Chem., Vol. 35, 1198 (1970)]. Furthermore, the esterification of such sterically hindered benzoic acid generally requires a strong acidic condition, and therefore, is not applicable to the synthesis of the compound of formula (I) according to the present invention.

In order to overcome such problems, the present inventors have developed a novel pyridine thio ester compound represented by the following general formula (II) as an intermediate useful for preparing the compound of formula (I) according to the present invention. Accordingly, the compound of the following general formula (II) also constitutes a further object of the present invention:

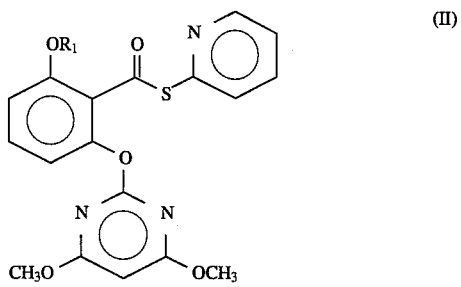

In the above formula (II), $R_1$ is defined as previously described in connection with the compound of formula (I).

The pyridine thio ester compound of formula (II), as defined above, is useful for synthesis of not only the imino ester compound of formula (I) according to the present invention, but also most ester compounds which can be hardly prepared according to conventional methods.

According to the present invention, the compound of formula (I) can be conveniently prepared by condensing the compound of formula (II), as defined above, with an oxime compound represented by the following general formula (III) in the presence of a metal salt:

In the above formula (III), $R_2$ and $R_3$ are defined as previously described in connection with the compound of formula (I).

The process for preparing the compound of formula (I) according to the present invention can be represented by the following reaction scheme A.

Reaction Scheme A

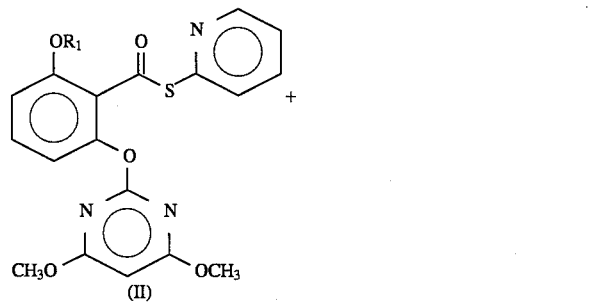

-continued
Reaction Scheme A

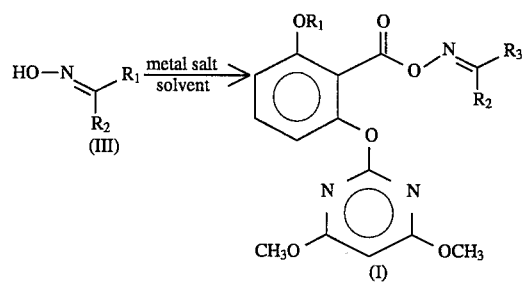

In the above reaction scheme, $R_1$, $R_2$ and $R_3$ are defined as previously described in connection with the compound of formula (I).

The reaction according to the reaction scheme A above can be conducted in a reaction-inert organic solvent in the presence of a metal salt. The reaction-inert organic solvent which can be suitably used in this reaction is preferably halogenated hydrocarbon solvents such as dichloromethane, chloroform, carbon tetrachloride, 1,2-dichloroethane, etc., or nitriles such as acetonitrile, propionitrile, etc. As the metal salt which can be used in this reaction, cuper (II) salts such as cupric chloride, cupric bromide, etc., can be mentioned. This reaction can be carried out at either elevated temperature or normal temperature.

The novel pyridine thio ester compound of formula (II) which is used as the starting material in the reaction scheme A according to the present invention can be synthesized from the known benzoic acid compound of formula (IV) (see European Patent Publication No. 321,846), as depicted in the following reaction scheme B.

Reaction Scheme B

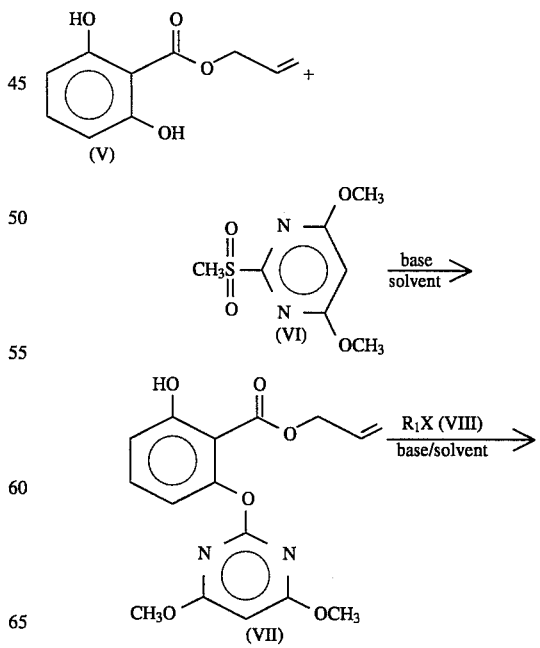

-continued
Reaction Scheme B

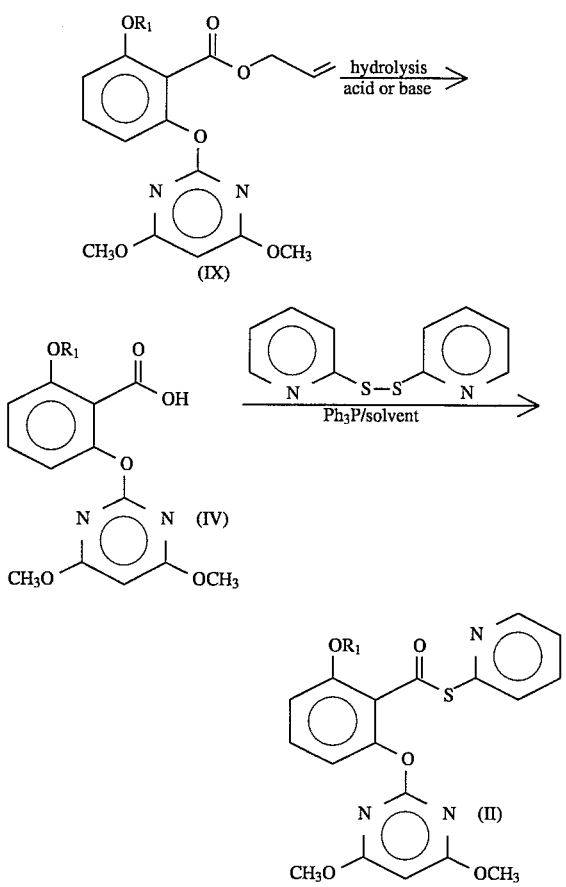

In the above reaction scheme, $R_1$ is defined as previously described in connection with the compound of formula (I), and X represents a halogen atom.

Hereinafter, the process for preparing the novel compound of formula (II) according to the reaction scheme B will be specifically explained step by step.

First, in the first reaction step the compound of formula (V) is reacted with the compound of formula (VI) in the presence of a reaction-inert organic solvent and a base to obtain the compound of formula (VII). As the base for this reaction, alkali metal hydrides such as potassium hydride, sodium hydride, etd., or alkali metal carbonates or bicarbonates such as potassium carbonate, potassium bicarbonate, sodium carbonate, sodium bicarbonate, etc. can be preferably used; and as the solvent a hydrocarbon solvent such as tetrahydrofuran, dioxane, methylethylketone, etc., a polar solvent such as dimethylformamide, dimethylsulfoxide, acetonitrile, etc. can be preferably used. In this reaction, each of the compound of formula (VI) and the base is preferably used in the ratio of one equivalent weight with respect to the compound of formula (V). The reaction of the first step can be carried out at either normal temperature or elevated temperature.

In the second step of the reaction scheme B, the compound of formula (VII) produced in the first step is reacted with the compound of formula (VIII) in an appropriate solvent in the presence of an appropriate base at the temperature between room temperature and 120° C. for 1 to 24 hours to produce the compound of formula (IX). As the base suitable for this reaction, sodium hydride, potassium hydride, potassium bicarbonate, sodium carbonate, etc. can be mentioned. In this reaction, as the solvent, methylene chloride, acetonitrile, tetrahydrofuran, dimethylformamide, and the like can be used.

In the third step of the reaction scheme B, the compound of formula (IX) produced in the second step is hydrolysed with an acid or a base to obtain the compound of formula (IV) which is subsequently then reacted with an equimolar amount of 2,2'-dipyridylsulfide and triphenylphosphine ($Ph_3P$) in the presence of a suitable solvent to produce the desired novel compound of formula (II). As the solvent suitable for this reaction, a hydrocarbon solvent such as benzene, toluene, xylene, acetonitrile, dichloromethane, etc., can be preferably used.

The present invention will be more specifically explained by the following examples. However, it should be understood that the present invention is not restricted to these examples in any manner.

Preparation 1

Synthesis of 6-hydroxy-2-(4,6-dimethoxypyrimidin-2-yl)oxybenzoic acid allyl ester (VII)

2.0 g of allyl 2,6-dihydroxybenzoate (V) was added to the suspension of 0.4 g of sodium hydride in 50 ml of dimethylformamide and the mixture was stirred for 10 minutes. To this mixture was added 2.2 g of 4,6-dimethoxy-2-methylsulfonylpyrimidine. The reaction mixture was stirred for 5 hours and 50 ml of saturated ammonium chloride solution was added thereto. The reaction solution was then extracted with 200 ml of ethylacetate. The extract was dried over anhydrous sodium sulfate and then distilled under reduced pressure to remove the solvent. The residue was subjected to column chromatography (hexane:ethylacetate= 2:1 v/v) on silica gel to obtain 3.0 g (Yield 90%) of the title compound.

$^1$H NMR (CDCl$_3$, δ): 3.81(s, 6H), 4.58(d, 2H), 5.11–5.29(d, 2H), 5.51–5.70(m, 1H), 5.73(s, 1H), 6.68–7.47(m, 3H), 11.12(s, 1H)

Preparation 2

Synthesis of 6-methoxy-2-(4,6-dimethoxypyrimidin-2-yl)oxybenzoic acid allyl ester(IX-1) (IX, $R_1$=Me)

3.3 g of the compound (VII) prepared by Preparation 1, 1.4 g of methyl iodide and 1.4 g of potassium carbonate were added to 200 ml of dimethylformamide and the mixture was stirred for 12 hours. Then the solvent was distilled off under reduced pressure. To the residue was added 50 ml of ethylacetate and the mixture was washed with water. The organic layer was separated, dried over anhydrous sodium sulfate and then distilled under reduced pressure to remove the solvent. The residue was subjected to column chromatography (hexane:ethylacetate=2:1 v/v) on silica gel to obtain 3.2 g (Yield 92%) of the title compound.

$^1$H NMR (CDCl$_3$, δ): 3.79(s, 6H), 3.90(s, 3H), 4.59(d, 2H), 5.13–5.30(d, 2H), 5.52–5.72(m, 1H), 5.75 (s, 1H), 6.70–7.45(m, 3H)

According to the same procedure, the compounds (IX-2, $R_1$=Et), (IX-3, $R_1$=allyl), (IX-4, $R_1$=acetyl), (IX-5, $R_1$=methanesulfonyl), (IX-6, $R_1$=2-thiopenemethyl) and (IX-7, $R_1$=2-furylmethyl) were prepared from the compound of formula (VII).

Preparation 3

Synthesis of 6-methoxy-2-(4,6-dimethoxypyrimidin-2-yl)oxybenzoic acid 2-pyridine thio ester (II-1) (II, R$_1$=Me)

3.5 g of the allyl ester compound (IX-1) prepared by Preparation 2 was added to 20 ml of 2N sodium hydroxide solution and then stirred for 12 hours. The reaction solution was neutralized with 6N hydrochloric acid solution. The precipitated solid product was filtered and then dried to obtain the benzoic acid derivative (IV-1, R$_1$=Me). 3.0 g of the resulting compound (IV-1), 2.2 g of 2,2-dipyridyldisulfide and 2.6 g of triphenylphosphine were added to 50 ml of toluene and then vigorously stirred for 3 hours at normal temperature. The reaction mixture was distilled under reduced pressure to remove the solvent, and the residue was subjected to column chromatography (hexane:ethylacetate= 2:1 v/v) on silica gel to obtain 3.6 g (Yield 90%) of the title compound (II-1) as a white solid.

$^1$H NMR (CDCl$_3$, δ): 3.80(s, 6H), 3.91(s, 3H), 5.76(s, 1H), 6.85–7.65(m, 6H), 8.58(d, 1H)

The compounds (II-2) to (II-7) were prepared according to the same procedure as Preparation 3 and their physical properties are given in the following.

$^1$H NMR (CDCl$_3$, δ) of the compound (II-2, R$_1$=ethyl): 1.46–1.54(t, 3H), 3.82(s, 6H), 4.21–4.29(q, 2H), 5.77(s, 1H), 6.88–7.55(m, 6H), 8.57(d, 1H)

$^1$H NMR (CDCl$_3$, δ) of the compound (II-3, R$_1$=allyl): 3.81(s, 6H), 4.64–4.66(d, 2H), 5.28–5.47(d, 2H), 5.75(s, 1H), 5.98–6.02(m, 1H), 6.83–7.67(m, 6H), 8.57(d, 1H)

$^1$H NMR (CDCl$_3$, δ) of the compound (II-4, R$_1$=acetyl): 2.25(s, 3H), 3.80(s, 6H), 5.76(s, 1H), 7.08–7.70(m, 6H), 8.56(d, 1H)

$^1$H NMR (CDCl$_3$, δ) of the compound (II-5, R$_1$=methanesulfonyl): 3.27(s, 3H), 3.84(s, 6H), 5.83(s, 1H), 7.21–7.79(m, 6H), 8.58(d, 1H)

$^1$H NMR (CDCl$_3$, δ) of the compound (II-6, R$_1$=thienylmethyl): 3.82(s, 6H), 5.35(s, 2H), 5.76(s, 1H), 6.88–7.68(m, 6H), 8.55(d, 1H)

$^1$H NMR (CDCl$_3$, δ) of the compound (II-7, R$_1$=furylmethyl): 3.82(s, 6H), 5.13(s, 2H), 5.76(s, 1H), 6.32–7.66(m, 6H), 8.56(d, 1H)

Preparation 4

Synthesis of 2,6-di(4,6-dimethoxypyrimidin-2-yl)oxybenzoic acid 2-pyridine thio ester (II-8) (II, R$_1$=4,6-dimethoxy-2-pyrimidinyl)

48.0 g of the known compound 2,6-di(4,6-dimethoxypyrimidin-2-yl)oxybenzoic acid, 22.0 g of 2,2'-dipyridyldisulfide and 26.2 g of triphenylphosphine were added to 250 ml of toluene and then vigorously stirred for 3 hours at normal temperature. The reaction mixture was filtered, and then the filtrate was distilled under reduced pressure to remove toluene. The residue was subjected to column chromatography (hexane:ethylacetate=2:1 v/v) on silica gel to obtain 42.0 g (Yield 90%) of the title compound (II-8) as a white solid.

$^1$H NMR (CDCl$_3$, δ): 3.77(s, 6H), 6.03(s, 2H), 7.32–7.87(m, 6H), 8.54–8.55(d, 1H)

Preparation 5

Synthesis of benzaldehyde oxime (III-1)

10.6 g of benzaldehyde, 7.0 g of hydroxylamine hydrochloride and 14.0 g of sodium carbonate were added to 200 ml of methanol and then stirred for 5 hours at normal temperature. The reaction mixture was filtered and then methanol was distilled off under reduced pressure from the filtrate to obtain 12.0 g (Yield 99%) of the title compound (III-1) as a white solid.

According to the same procedure as Preparation 5, the benzaldehyde oxime compounds of formula (III) having different substituents could be readily prepared from the corresponding benzaldehyde compounds.

Preparation 6

Synthesis of methylpyruvate oxime (III-4)

10.2 g of methyl pyruvate, 7.0 g of hydroxylamine hydrochloride and 14.0 g of potassium carbonate were added to 200 ml of methanol and then stirred for 5 hours at normal temperature. The reaction mixture was filtered and then methanol was distilled off under reduced pressure from the filtrate to obtain 10.1 g (Yield 99%) of the title compound (III-4) as a white solid.

EXAMPLE 1

Synthesis of the compound (1) (I, R$_1$=4,6-dimethoxy-2-pyrimidinyl, R$_2$=H, R$_3$=H)

1.2 g of benzaldehyde oxime (III-1) prepared by Preparation 5 and 4.0 g of the pyridine thio ester compound (II-8) prepared by Preparation 4 were dissolved in 50 ml of dichloromethane and the mixture was stirred at normal temperature for 5 minutes. To this mixture was added 2.2 g of cupric bromide and the reaction mixture was then stirred for further one hour and filtered. The filtrate was concentrated and then the residue was subjected to column chromatography (hexane:ethylacetate=2:1 v/v) on silica gel to obtain 3.4 g (Yield 85%) of the title compound (1).

EXAMPLE 2

Synthesis of the compound (58) (I, R$_1$=Me, R$_2$=H, R$_3$=3-methylphenyl)

4.0 g of the pyridine thio ester compound (II-1) prepared by Preparation 3 and 1.4 g of the known compound 3'-methylbenzaldehyde oxime (III-2) were dissolved in 50 ml of methylene chloride. While the reaction solution is stirred at normal temperature, 2.2 g of cupric bromide was added thereto. The reaction mixture was stirred for further one hour and then filtered. The filtrate was distilled under reduced pressure and then the residue was subjected to column chromatography (hexane:ethylacetate=2:1 v/v) on silica gel to obtain 3.7 g (Yield 90%) of the title compound (58).

EXAMPLE 3

Synthesis of the compound (65) (I, R$_1$=allyl, R$_2$=Me, R$_3$=phenyl)

4.2 g of the pyridine thio ester compound (II-3) prepared by Preparation 3 and 1.4 g of the known compound acetophenone oxime were dissolved in 50 ml of methylene chloride. While this mixture is stirred at normal temperature, 2.2 g of cupric bromide was added thereto. The reaction mixture was stirred for further 30 minutes and then filtered. The filtrate was distilled under reduced pressure to remove the solvent and then the residue was subjected to column chromatography (hexane:ethylacetate=2:1 v/v) on silica gel to obtain 3.2 g (Yield 80%) of the title compound (65).

EXAMPLE 4

Synthesis of the compound (48) (I, $R_1$=4,6-dimethoxy-2-pyrimidinyl, $R_2$=$CH_3$, $R_3$=$COOCH_3$)

1.0 g of methylpyruvate oxime (III-4) prepared by Preparation 6 and 4.0 g of the thio ester compound (II-8) prepared by Preparation 4 were dissolved in 50 ml of dichloromethane and the mixture was stirred at normal temperature for 5 minutes. To this mixture was added 2.2 g of cupric bromide and the reaction mixture was then stirred for further one hour and filtered. The filtrate was concentrated and then the residue was subjected to column chromatography (hexane:ethylacetate=2:1 v/v) on silica gel to obtain 3.4 g (Yield 85%) of the title compound (48).

The compounds given in the above Tables 1 to 3 could be prepared according to the same procedure as Examples 1 to 4. The physical properties of the prepared compounds are given in the following Table 4.

TABLE 4

| Comp. No. | $^1$H NMR (CDCl$_3$) δ ppm | MS (FAB) | m.p. (°C.) |
|---|---|---|---|
| 1 | 3.78 (s, 12H), 5.73(s, 2H), 7.20–7.61(m, 8H), 8.09(s, 1H) | 534 | 60–65 |
| 2 | 3.79(s, 12H), 5.73(s, 2H), 7.22–7.98(m, 7H), 8.52(s, 1H) | 568 | |
| 3 | 3.79(s, 12H), 5.74(s, 2H), 7.21–7.62(m, 7H), 8.06(s, 1H) | 568 | |
| 4 | 3.78(s, 12H), 5.73(s, 2H), 7.20–7.59(m, 7H), 8.06(s, 1H) | 568 | 173–174 |
| 5 | 3.79(s, 6H), 5.73(s, 2H), 7.0–8.0(m, 7H), 8.35(s, 1H) | 552 | |
| 6 | 3.78(s, 12H), 5.72(s, 2H), 7.04–7.62(m, 7H), 8.06(s, 1H) | 552 | |
| 7 | 2.35(s, 3H), 3.79(s, 12H), 5.73(s, 2H), 7.16–7.70(m, 7H), 8.33(s, 1H) | 548 | 131–133 (dec.) |
| 8 | 2.34(s, 3H), 3.78(s, 12H), 5.73(s, 2H), 7.20–7.63(m, 7H), 8.06(s, 1H) | 548 | |
| 9 | 2.37(s, 3H) , 3.78(s, 12H), 5.72(s, 2H), 7.14–7.63(m, 7H), 8.06(s, 1H) | 548 | 115–119 |
| 10 | 3.79(s, 12H), 3.84(s, 3H), 5.73(s, 2H), 6.87–8.86(m, 7H), 8.45(s, 1H) | 564 | |
| 11 | 3.78(s, 12H), 3.81(s, 3H), 5.73(s, 2H), 6.94–7.63(m, 7H), 8.05(s, 1H) | 564 | |
| 12 | 3.78(s, 12H), 3.82(s, 3H), 5.73(s, 2H), 6.84–7.62(m, 7H), 8.04(s, 1H) | 564 | 126–129 |
| 13 | 1.23(t, 3H), 3.77(s, 12H), 4.05(q, 2H), 5.74(s, 2H), 6.80–7.60(m, 7H), 8.50(s, 1H) | 578 | |
| 14 | 1.25(t, 3H), 3.76(s, 12H), 4.05(q, 2H), 5.73(s, 2H), 6.80–7.60(m, 7H), 8.02(s, 1H) | 578 | |
| 15 | 3.78(s, 12H), 4.57(d, 2H), 5.2–5.4(m, 2H), 5.73(s, 2H), 5.9–6.1(m, 1H), 6.8–7.9(m, 7H), 8.50(s, 1H) | 590 | |
| 16 | 0.94–1.10(t, 3H), 1.44–1.53(q, 2H), 1.74–1.79(q, 2H), 3.75(s, 12H), 3.95–4.00(t, 2H), 5.72(s, 2H), 6.85–7.60(m, 7H), 8.00(s, 1H) | 606 | |
| 17 | 3.78(s, 12H), 5.12(s, 2H), 5.75(s, 2H), 6.9–7.6(m, 12H), 8.02(s, 1H) | 640 | |
| 18 | 3.77(s, 12H), 5.73(s, 2H), 6.80–7.70(m, 12H), 8.02(s, 1H) | 626 | |
| 19 | 3.78(s, 12H), 5.73(s, 2H), 6.9–7.6(m, 12H), 8.05(s, 1H) | 626 | |
| 20 | 2.51(s, 3H), 3.78(s, 12H), 5.73(s, 2H), 6.80–7.70(m, 7H), 8.20(s, 1H) | 580 | |
| 21 | 3.77(s, 12H), 5.74(s, 2H), 6.80–7.80(m, 7H), 8.05(s, 1H) | 559 | |
| 22 | 3.79(s, 12H), 5.74(s, 2H), 7.21–8.27(m, 8H) | 579 | |
| 23 | 2.32(s, 3H), 3.77(s, 12H), 5.73(s, 2H), 6.80–7.60(m, 5H), 7.72(d, 2H), 8.20(s, 1H) | 592 | |
| 24 | 2.26(s, 3H), 3.78(s, 12H), 5.73(s, 2H), 7.19–7.62(m, 8H) | 548 | 85–94 |
| 25 | 3.79(s, 12H), 3.87(s, 3H), 5.71(s, 2H), 7.12–7.67(m, 8H) | 564 | 150–158 (dec.) |
| 26 | 1.95(s, 3H), 3.78(s, 12H), 5.74(s, 2H),7.18–7.60(m, 8H) | 580 | 116–118 |
| 27 | 3.79(s, 12H), 5.74(s, 2H), 7.21–7.82(m, 8H) | 568 | |
| 28 | 3.72(s, 12H), 5.72(s, 2H), 7.10–7.48(m, 13H) | 610 | 128–130 |
| 29 | 3.72(s, 12H), 5.72(s, 2H), 7.22–7.98(m, 8H) | 559 | 160–165 (dec.) |
| 30 | 3.03(s, 6H), 3.78(s, 12H), 5.74(s, 2H), 6.66(d, 2H), 6.70–7.60(m, 5H), 8.10(s, 1H) | 577 | |
| 31 | 3.79(s, 12H), 3.95(s, 3H), 5.74(s, 2H), 7.14–7.67(m, 8H) | 592 | |
| 32 | 1.30–1.36(t, 3H), 2.34(s, 3H), 3.80(s, 12H), 4.38–4.48(q, 2H), 5.75(s, 2H), 7.17–7.62(m, 7H) | 620 | |
| 33 | 0.95–1.00(t, 3H), 1.71–1.80(q, 2H), 3.42–3.52(q, 2H), 3.71(s, 12H), 5.72(s, 2H), 7.17–7.67(m, 8H), 8.21–8.27(t, 1H) | 619 | |
| 34 | 2.89(s, 3H), 2.98(s, 3H), 3.70(s, 12H), 5.68(s, 2H), 7.17–7.84(m, 8H) | 605 | |
| 35 | 3.63(s, 12H), 4.71–4.73(d, 2H), 5.69(s, 2H), 7.14–7.69(m, 13H), 8.68–8.72(t, 1H) | 668 | |
| 36 | 3.63(s, 12H), 4.69–4.72(d, 2H), 5.69(s, 2H), 7.13–7.64(m, 12H), 8.69–8.74(t, 1H) | 703 | |
| 37 | 3.62(s, 12H), 3.81(s, 3H), 4.70–4.72(d, 2H), 5.68(s, 2H), 6.83–7.65(m, 12H), 8.62–8.69(t, 1H) | 670 | |
| 38 | 3.63(s, 12H), 3.77(s, 3H), 4.67–4.71(d, 2H), 5.70(s, 2H), 6.87–7.65(m, 2H), 8.63–8.69(t, 1H) | 670 | |
| 39 | 3.68(s, 12H), 4.47–4.69(d, 2H), 5.68(s, 2H), 7.08–7.68(m, 12H), 8.70–8.81(t, 1H) | 701 (H$^+$) | |
| 40 | 2.29(s, 3H), 3.64(s, 12H), 4.64–4.68(d, 2H), 5.69(s, 2H), 6.99–7.69(m, 2H), 8.54–8.53(t, 1H) | 682 | |
| 41 | 3.65(s, 12H), 3.79(s, 3H), 4.42–4.66(d, 2H), 5.68(s, 2H), 6.71–6.89(d, 2H), 7.13–7.68(m, 10H), 8.42–8.68(t, 1H) | 697 (M + 1) | |
| 42 | 3.65(s, 12H), 3.72(s, 3H), 4.46–4.71(d, 2H), 5.68(s, 2H), 6.75–7.70(m, 12H), 8.45–8.70(t, 1H) | 697 (M + 1) | |
| 43 | 3.68(s, 12H), 4.71–4.73(d, 2H), 5.70 (s, 2H), 6.26–6.31(m, 2H), 7.13–7.68(m, 9H), 7.76–7.80(t, 1H) | 658 | |
| 44 | 3.01(t, 2H), 3.65(t, 2H), 3.72(s, 12H), 7.03–7.69(m, 13H), 8.40–8.70(t, 1H) | 681 (M + 1) | |
| 45 | 3.80(s, 12H), 3.84(s, 3H), 5.74(s, 2H), 7.1–7.7(m, 3H), 7.55(s, 1H) | 516 | |
| 46 | 1.32–1.35(t, 3H), 3.79(s, 12H), 4.30–4.33(q, 2H), 5.74(s, 2H), 7.19–7.22(d, 2H), 7.56(s, 1H), 7.58–7.62(t, 1H) | 530 (M + 1) | |
| 47 | 1.94(s, 3H), 2.37(s, 3H), 3.79(s, | 514 | 119–121 |

TABLE 4-continued

| Comp. No. | ¹H NMR (CDCl₃) δ ppm | MS (FAB) | m.p. (°C.) |
|---|---|---|---|
|  | 12H), 5.75(s, 2H), 7.19–7.22(d, 2H), 7.57–7.63(t, 1H) |  | (dec.) |
| 48 | 2.13(s, 3H), 3.81(s, 12H), 3.85(s, 3H), 5.76(s, 2H), 7.20–7.23(d, 2H), 7.54–7.61(t, 1H) | 530 | 176–179 (dec.) |
| 49 | 2.09(s, 3H), 3.77(s, 12H), 5.27(s, 2H), 5.71(s, 2H), 7.17–7.20(d, 2H), 7.35(m, 5H), 7.54–7.61(t, 1H) | 606 | 134–136 |
| 50 | 2.06(s, 3H), 3.77(s, 12H), 4.44–4.46(d, 2H), 5.70(s, 2H), 7.18–7.32(m, 7H), 7.55–7.61(t, 1H) | 605 |  |
| 51 | 0.88(t, 3H), 2.55(q, 2H), 3.79(s, 12H), 3.84(s, 3H), 5.71(s, 2H), 7.2–7.6(m, 3H) | 544 |  |
| 52 | 1.09–1.12(d, 6H), 1.28–1.33(t, 3H), 3.14–3.28(q, 1H), 3.79(s, 12H), 4.22–4.29(q, 2H), 5.75(s, 2H), 7.16–7.19(d, 2H), 7.54–7.60(t, 1H) | 572 |  |
| 53 | 0.84–0.89(t, 3H), 1.23–1.42(m, 7H), 2.53–2.59(t, 2H), 3.79(s, 12H), 4.23–4.33(q, 2H), 5.75(s, 2H), 7.17–7.21(d, 2H), 7.54–7.60(t, 1H) | 586 | 104–105 |
| 54 | 0.8–1.4(m, 7H), 2.55(t, 2H), 3.79(s, 12H), 5.25(s, 2H), 7.2–7.6(m, 8H) | 648 |  |
| 55 | 0.8–1.4(m, 7H), 2.55(t, 2H), 3.79(s, 2H), 4.45(d, 2H), 7.2–7.6(m, 8H) | 647 |  |
| 56 | 0.81–0.85(t, 3H), 1.22–1.49(m, 9H), 2.49–2.52(t, 2H), 3.78(s, 12H), 4.24–4.31(q, 2H), 5.73(s, 2H), 7.16–7.19(d, 2H), 7.54–7.60(t, 1H) | 510 |  |
| 57 | 0.83–0.89(t, 3H), 1.23–1.46(m, 15H), 2.52–2.56(t, 2H), 3.79(s, 12H), 4.25–4.32(q, 2H), 5.75(s, 2H), 7.17–7.20(d, 2H), 7.54–7.60(t, 1H) | 642 |  |
| 58 | 2.40(s, 3H), 3.82(s, 3H), 3.93(s, 3H), 5.77(s, 1H), 6.80–7.50(m, 7H), 8.23(s, 1H) | 424 |  |
| 59 | 2.31(s, 3H), 3.82(s, 6H), 3.93(s, 3H), 5.77(s, 1H), 6.87–6.92(m, 2H), 7.30–7.76(m, 6H) | 424 |  |
| 60 | 1.98(s, 3H), 3.83(s, 6H), 3.91(s, 3H), 5.75(s, 1H), 6.84–6.90(m, 2H), 7.41–7.46(m, 6H) | 456 |  |
| 61 | 1.21–1.27(t, 3H), 2.63–2.72(q, 2H), 3.79(s, 6H), 3.90(s, 3H), 5.75(s, 1H), 6.84–6.90(m, 2H), 7.22–7.63(m, 5H), 8.20(s, 1H) | 438 |  |
| 62 | 1.39–1.45(t, 3H), 2.29(s, 3H), 3.80(s, 6H), 4.10–4.18(q, 2H), 5.75(s, 1H), 6,83–6.88(m, 2H), 7.35–7.44(m, 4H), 7.71–7.74(m, 2H) | 438 |  |
| 63 | 1.39–1.45(t, 3H), 1.97(s, 3H), 3.81(s, 6H), 4.08–4.16(q, 2H), 5.75(s, 1H), 6.82–6.87(m, 2H), 7.31–7.43(m, 6H) | 470 |  |
| 64 | 1.22–1.27(t, 3H), 1.39–1.44(t, 3H), 2.64–2.72(q, 2H), 3.79(s, 6H), 4.09–4.12(q, 2H), 5.75(s, 1H), 6.82–6.88(m, 2H), 7.22–7.63(m, 5H), 8.20(s, 1H) | 452 |  |
| 65 | 2.28(s, 3H), 3.80(s, 6H), 4.63–4.65(d, 1H), 5.23–5.46(d, 2H), 5.74(s, 2H), 5.95–6.15(m, 1H), 6.83–6.90(m, 2H), 7.27–7.72(m, 6H) | 450 |  |
| 66 | 1.98(s, 3H), 3.83(s, 6H), 4.65–4.67(d, 2H), 5.23–5.74(d, 2H), 5.75(s, 1H), 5.96–6.16(m, 1H), 6.86(m, 2H), 7.42(m, 6H) | 482 |  |
| 67 | 3.79(s, 6H), 4.63–4.64(d, 2H), 5.23–5.47(d, 2H), 5.94–6.14(m, 1H), 6.83–6.91(m, 2H), 7.38–7.70(m, 6H), 8.24(s, 1H) | 436 |  |
| 68 | 3.81(s, 6H), 4.67–4.69(d, 2H), 5.25–5.48(d, 2H), 5.76(s, 1H), 5.97–6.15(m, 1H), 6.86–6.93(m, 2H), 7.44–7.51(m, 4H), 7.93–7.96(m, 2H) | 461 |  |
| 69 | 3.74(s, 6H), 3.92(s, 3H), 4.56–4.58(d, 2H), 5.22–5.46(d, 2H), 5.72(s, 1H), 5.86–6.05(m, 1H), 6.76–6.64(m, 2H), 7.34–7.53(m, 6H) | 494 |  |
| 70 | 2.41(s, 3H), 3.82(s, 6H), 5.80(s, 1H), 7.13–7.76(m, 8H), 8.27(s, 1H) | 438 |  |
| 71 | 3.29(s, 3H), 3.79(s, 6H), 5.77(s, 1H), 7.42–7.68(m, 8H), 8.23(s, 1H) | 474 |  |
| 72 | 3.79(s, 6H), 5.33(s, 2H), 5.75(s, 1H), 6.93–7.69(m, 8H), 8.20(s, 1H) | 492 |  |
| 73 | 3.79(s, 6H), 5.11(s, 2H), 5.75(s, 1H), 6.34–6.43(m, 2H), 6.91–7.01 (m, 2H), 7.40–7.69(m, 4H), 8.19 (s, 1H) | 476 |  |

When the compound of formula (I) according to the present invention is used as a herbicide, the compound can be used as it is or as formulated in various formulations such as a solution, an emulsion, a powder or a granule by blending it with a solid carrier such as clay, talc, diatomaceous earth, etc., or a liquid carrier such as water, alcohol, benzene, toluene, ether, ketones, esters, acids, amides, etc., and optionally with conventional adjuvants such as an emulsifying agent, a dispersing agent, a penetrating agent, an adhesive, a stabilizer, etc.

The specific examples of the herbicidal formulation containing the compound of formula (I) according to the present invention as an active ingredient are illustrated in the following. However, it should be understood that the present invention is not limited to these examples in any manner.

Formulation Example 1 (upland field condition, 500 g/ha)

160 mg of the compound according to the present invention was dissolved in 640 ml of the organic solvent (acetone) and the resulting solution was diluted with 640 ml of distilled water containing 0.2% of a non-ionic surfactant, Tween 20, to obtain the desired formulation.

Formulation Example 2 (upland field condition, 16 g/ha)

5 mg of the compound according to the present invention was dissolved in 640 ml of the organic solvent (acetone) and the resulting solution was diluted with 640 ml of distilled water containing 0.2% of a non-ionic surfactant, Tween 20, to obtain the desired formulation.

Formulation Example 3 (paddy field condition, 250 g/ha)

80 mg of the compound according to the present invention was dissolved in 320 ml of the organic solvent (acetone) and the resulting solution was diluted with 320 ml of distilled water containing 0.2% of a non-ionic surfactant, Tween 20, to obtain the desired formulation.

As previously described, the compound of formula (I) according to the present invention is useful as a herbicide. The herbicidal activity of the compound of formula (I) according to the present invention was examined according to a pot culture and treatment method of test plants in greenhouse. The herbicidal activity and phytotoxicity were determined in accordance with the evaluation standard as identified in the following Table 5.

TABLE 5

| Index No. | Evaluation standard of herbicidal activity and phytotoxicity | |
|---|---|---|
| | Herbicidal Activity | Phytotoxicity |
| 0 | 0% | 0% |
| 1 | 10–20% | 10–20% |
| 2 | 30–40% | 30–40% |
| 3 | 50–60% | 50–60% |
| 4 | 70–80% | 70–80% |
| 5 | 90–100% | 90–100% |

As the test plants for determining the herbicidal activity and phytotoxicity of the compound of formula (I) according to the present invention in the following test examples, weeds grown in upland field such as *Digitaria sanquinalis, Alopecurus aequallis, Setaria farberi, Echinochloa crusgalli var. caudata, Amaranthus retroflexus, Aeschynomene indica, Solanum nigrum, Abutilon theophrasti, Xanthium strumarium, Calystegia japonica, Panicum dichotomiflorum* and *Sorghum bicolor*, weeds grown in paddy field such as *Echinochloa crus-qalli vat. oryzicola, Eleocharis kuroquwai, Saqittaria trifolia* and *Sagittaria pygmaea*, and crops such as cotton (*Gosshipium hirsutum*), wheat (*Triticum aestivum*) and rice plant (*Oryza sativar*) were used.

Test Example 1

Pre-emergence herbicidal activity with soil treatment (upland field condition)

Squarish plastic pots (20×15×10 cm) were filled with sterilized upland field soil (sandy-loam, pH 5.5–6.0) and then six (6) kinds of the seeds of upland weeds per pot having the surface area of 300 cm² were sown and covered with soil of a thickness of 0.5 cm. After the pot is submerged with water for one day, the predetermined amount of the solution of Formulation Example 1 which corresponds to the applied amount of 500 g of the active ingredient per hectare was uniformly applied to the soil surface. The test plants were observed for 30 days after the treatment with the test formulation and then the herbicidal activity of the test compounds was evaluated on the basis of the evaluation standard as described in Table 5 above. The results are given in the following Table 6.

In the following tables, the abbreviations of the test plants denote the following:

Dig: Digitaria sanquinalis
Alo: Alopecurus aequallis
Set: Setaria farberi
Ech: Echinochloa crus-galli var. caudata
Ama: Amaranthus retroflexus
Aes: Aeschynomene indica
Sol: Solanum nigrum
Abu: Abutilon theophrasti
Xan: Xanthium strumarium
Cal: Calystegia japonica
Pan: Panicum dichotomiflorum
Sor: Sorghum bicolor
Ecg: Echinochloa crus-galli var. oryzicola
Ele: Eleocharis kuroguwai
Sag: Sagittaria trifolia
Sap: Sagittaria pygmaea
Cot: cotton (Gosshipium hirsutum)
Whe: wheat (Triticum aestivum)
Ric: rice plant(Oryza sativar)

TABLE 6

| Comp. No. | Herbicidal Activity | | | | | |
|---|---|---|---|---|---|---|
| | Sol | Ama | Xan | Dig | Pan | Ech |
| 1 | 5 | 5 | 5 | 5 | 5 | 5 |
| 2 | 5 | 5 | 5 | 5 | 5 | 5 |
| 3 | 5 | 5 | 5 | 5 | 5 | 5 |
| 4 | 5 | 5 | 5 | 5 | 5 | 5 |
| 5 | 5 | 5 | 5 | 5 | 5 | 5 |
| 6 | 5 | 5 | 5 | 5 | 5 | 5 |
| 7 | 5 | 5 | 5 | 5 | 5 | 5 |
| 8 | 5 | 5 | 5 | 5 | 5 | 5 |
| 9 | 5 | 5 | 5 | 4 | 5 | 5 |
| 10 | 5 | 5 | 5 | 5 | 5 | 5 |
| 11 | 5 | 5 | 5 | 5 | 5 | 5 |
| 12 | 5 | 5 | 5 | 5 | 5 | 5 |
| 13 | 5 | 5 | 5 | 5 | 5 | 5 |
| 14 | 5 | 5 | 5 | 5 | 5 | 5 |
| 15 | 5 | 5 | 5 | 5 | 5 | 5 |
| 16 | 5 | 5 | 5 | 5 | 5 | 5 |
| 17 | 5 | 5 | 5 | 5 | 5 | 5 |
| 18 | 5 | 5 | 5 | 4 | 5 | 5 |
| 19 | 5 | 5 | 5 | 5 | 5 | 5 |
| 20 | 5 | 5 | 5 | 5 | 5 | 5 |
| 21 | 5 | 5 | 5 | 5 | 5 | 5 |
| 22 | 5 | 5 | 5 | 5 | 5 | 5 |
| 23 | 5 | 5 | 5 | 5 | 5 | 5 |
| 24 | 5 | 5 | 5 | 5 | 5 | 5 |
| 25 | 5 | 5 | 5 | 5 | 5 | 5 |
| 26 | 5 | 5 | 5 | 5 | 5 | 5 |
| 27 | 5 | 5 | 5 | 5 | 5 | 5 |
| 28 | 5 | 5 | 5 | 5 | 5 | 5 |
| 29 | 5 | 5 | 5 | 5 | 5 | 5 |
| 30 | 5 | 5 | 5 | 5 | 5 | 5 |
| 31 | 5 | 5 | 5 | 5 | 5 | 5 |
| 32 | 5 | 5 | 5 | 5 | 5 | 5 |
| 33 | 5 | 5 | 5 | 4 | 5 | 4 |
| 34 | 5 | 5 | 5 | 4 | 5 | 4 |
| 35 | 5 | 5 | 5 | 5 | 5 | 5 |
| 36 | 5 | 5 | 5 | 5 | 5 | 5 |
| 37 | 5 | 5 | 5 | 5 | 5 | 5 |
| 38 | 5 | 5 | 5 | 5 | 5 | 5 |
| 39 | 5 | 5 | 5 | 5 | 5 | 5 |
| 40 | 5 | 5 | 5 | 5 | 5 | 5 |
| 41 | 5 | 5 | 5 | 5 | 5 | 5 |
| 42 | 5 | 5 | 5 | 5 | 5 | 5 |
| 43 | 5 | 5 | 5 | 5 | 5 | 5 |
| 44 | 5 | 5 | 5 | 5 | 5 | 5 |
| 45 | 5 | 5 | 5 | 5 | 5 | 5 |
| 46 | 5 | 5 | 5 | 5 | 5 | 5 |
| 47 | 5 | 5 | 5 | 5 | 5 | 5 |
| 48 | 5 | 5 | 5 | 5 | 5 | 5 |
| 49 | 5 | 5 | 5 | 5 | 5 | 5 |
| 50 | 5 | 5 | 5 | 5 | 5 | 5 |
| 51 | 5 | 5 | 5 | 5 | 5 | 5 |
| 52 | 5 | 5 | 5 | 5 | 5 | 5 |
| 53 | 5 | 5 | 5 | 4 | 5 | 5 |
| 54 | 5 | 5 | 5 | 5 | 5 | 5 |
| 55 | 5 | 5 | 5 | 5 | 5 | 5 |
| 56 | 5 | 5 | 5 | 5 | 5 | 5 |
| 57 | 5 | 5 | 5 | 5 | 5 | 5 |

The same procedure as above was conducted by using the predetermined amount of the solution of Formulation Example 2 which corresponds to the applied amount of 63 g, 125 g or 250 g of the active ingredient per hectare to evaluate the herbicidal activity of the test compounds. The evaluated result is given in the following Table 7.

TABLE 7

| Comp. No. | Applied amount (g/ha) | Broad leaf weeds | | | | Narrow leaf weeds | | | |
|---|---|---|---|---|---|---|---|---|---|
| | | Cal | Sol | Abu | Ama | Dig | Pan | Ech | Sor |
| 58 | 63 | 5 | 5 | 5 | 5 | 5 | 5 | 5 | 5 |
| 59 | 63 | 5 | 5 | 5 | 5 | 5 | 5 | 5 | 5 |
| 60 | 63 | 5 | 5 | 5 | 5 | 5 | 5 | 5 | 5 |
| 61 | 63 | 5 | 5 | 5 | 5 | 5 | 5 | 5 | 5 |
| 62 | 63 | 5 | 5 | 5 | 5 | 5 | 5 | 5 | 5 |
| 63 | 63 | 5 | 5 | 5 | 5 | 5 | 5 | 5 | 5 |
| 64 | 63 | 5 | 5 | 5 | 5 | 5 | 4 | 4 | 5 |
| 65 | 125 | 5 | 5 | 5 | 5 | 5 | 5 | 5 | 5 |
| 66 | 125 | 4 | 5 | 4 | 5 | 4 | 3 | 3 | 5 |
| 67 | 125 | 5 | 5 | 5 | 5 | 4 | 4 | 5 | 5 |
| 68 | 125 | 4 | 5 | 5 | 5 | 4 | 5 | 4 | 5 |
| 69 | 125 | 5 | 5 | 5 | 5 | 5 | 5 | 4 | 5 |
| 70 | 250 | 4 | 5 | 4 | 5 | 3 | 4 | 3 | 5 |
| 71 | 250 | 4 | 4 | 3 | 5 | 3 | 4 | 3 | 5 |
| 72 | 250 | 3 | 4 | 4 | 4 | 5 | 2 | 3 | 5 |
| 73 | 250 | 5 | 5 | 5 | 4 | 4 | 4 | 4 | 5 |

Test Example 2

Post-emergence herbicidal activity with foliage treatment (upland field condition)

The test plants were sown according to the same procedure as Test Example 1 and then cultivated for 10 to 14 days. When the test plants grew to the 3 to 4-leaves stage, they were treated by uniformly spraying the predetermined amount of the solution of Formulation Example 1, which corresponds to the applied amount of 500 g of the active ingredient per hectare, to the foliage part of the plants. The test plants were observed for 30 days after spray treatment to determine the herbicidal activity of the test compounds. The results were evaluated on the basis of the standard as described in Table 5 above and are given in the following Table 8.

TABLE 8

| Comp. No. | Herbicidal Activity | | | | | |
|---|---|---|---|---|---|---|
| | Sol | Ama | Xan | Dig | Pan | Ech |
| 1 | 5 | 5 | 5 | 5 | 5 | 5 |
| 2 | 5 | 5 | 5 | 5 | 5 | 5 |
| 3 | 5 | 5 | 5 | 5 | 5 | 5 |
| 4 | 5 | 5 | 5 | 5 | 5 | 5 |
| 5 | 5 | 5 | 5 | 5 | 5 | 5 |
| 6 | 5 | 5 | 5 | 5 | 5 | 5 |
| 7 | 5 | 5 | 5 | 5 | 5 | 5 |
| 8 | 5 | 5 | 5 | 5 | 5 | 5 |
| 9 | 5 | 5 | 5 | 4 | 5 | 5 |
| 10 | 5 | 5 | 5 | 5 | 5 | 5 |
| 11 | 5 | 5 | 5 | 5 | 5 | 5 |
| 12 | 5 | 5 | 5 | 5 | 5 | 5 |
| 13 | 5 | 5 | 5 | 5 | 5 | 5 |
| 14 | 5 | 5 | 5 | 5 | 5 | 5 |
| 15 | 5 | 5 | 5 | 5 | 5 | 5 |
| 16 | 5 | 5 | 5 | 5 | 5 | 5 |
| 17 | 5 | 5 | 5 | 5 | 5 | 5 |
| 18 | 5 | 5 | 5 | 5 | 5 | 5 |
| 19 | 5 | 5 | 5 | 5 | 5 | 5 |
| 20 | 5 | 5 | 5 | 5 | 5 | 5 |
| 21 | 5 | 5 | 5 | 5 | 5 | 5 |
| 22 | 5 | 5 | 5 | 5 | 5 | 5 |
| 23 | 5 | 5 | 5 | 5 | 5 | 5 |
| 24 | 5 | 5 | 5 | 5 | 5 | 5 |
| 25 | 5 | 5 | 5 | 5 | 5 | 5 |
| 26 | 5 | 5 | 5 | 5 | 5 | 5 |
| 27 | 5 | 5 | 5 | 5 | 5 | 5 |
| 28 | 5 | 5 | 5 | 5 | 5 | 5 |
| 29 | 5 | 5 | 5 | 5 | 5 | 5 |
| 30 | 5 | 5 | 5 | 5 | 5 | 5 |
| 31 | 5 | 5 | 5 | 5 | 5 | 5 |
| 32 | 5 | 5 | 5 | 5 | 5 | 5 |
| 33 | 5 | 5 | 5 | 4 | 5 | 5 |
| 34 | 5 | 5 | 5 | 5 | 5 | 5 |
| 35 | 5 | 5 | 5 | 5 | 5 | 5 |
| 36 | 5 | 5 | 5 | 5 | 5 | 5 |
| 37 | 5 | 5 | 5 | 5 | 5 | 5 |
| 38 | 5 | 5 | 5 | 5 | 5 | 5 |
| 39 | 5 | 5 | 5 | 5 | 5 | 5 |
| 40 | 5 | 5 | 5 | 5 | 5 | 5 |
| 41 | 5 | 5 | 5 | 5 | 5 | 5 |
| 42 | 5 | 5 | 5 | 5 | 5 | 5 |
| 43 | 5 | 5 | 5 | 5 | 5 | 5 |
| 44 | 5 | 5 | 5 | 5 | 5 | 5 |
| 45 | 5 | 5 | 5 | 5 | 5 | 5 |
| 46 | 5 | 5 | 5 | 5 | 5 | 5 |
| 47 | 5 | 5 | 5 | 5 | 5 | 5 |
| 48 | 5 | 5 | 5 | 5 | 5 | 5 |
| 49 | 5 | 5 | 5 | 5 | 5 | 5 |
| 50 | 5 | 5 | 5 | 5 | 5 | 5 |
| 51 | 5 | 5 | 5 | 5 | 5 | 5 |
| 52 | 5 | 5 | 5 | 5 | 5 | 5 |
| 53 | 5 | 5 | 5 | 4 | 5 | 5 |
| 54 | 5 | 5 | 5 | 5 | 5 | 5 |
| 55 | 5 | 5 | 5 | 5 | 5 | 5 |
| 56 | 5 | 5 | 5 | 5 | 5 | 5 |
| 57 | 5 | 5 | 5 | 5 | 5 | 5 |

The same procedure as above was conducted by using the predetermined amount of the solution of Formulation Example 2 which corresponds to the applied amount of 63 g, 125 g or 250 g of the active ingredient per hectare to evaluate the herbicidal activity of the test compounds. The evaluated results are given in the following Table 9.

TABLE 9

| Comp. No. | Applied amount (g/ha) | Broad leaf weeds | | | | Narrow leaf weeds | | | |
|---|---|---|---|---|---|---|---|---|---|
| | | Cal | Sol | Abu | Ama | Dig | Pan | Ech | Sor |
| 58 | 63 | 5 | 5 | 5 | 5 | 5 | 5 | 5 | 5 |
| 59 | 63 | 5 | 5 | 5 | 5 | 5 | 5 | 5 | 5 |
| 60 | 63 | 5 | 5 | 5 | 5 | 5 | 5 | 5 | 5 |
| 61 | 63 | 5 | 5 | 5 | 5 | 5 | 5 | 5 | 5 |
| 62 | 63 | 5 | 5 | 5 | 5 | 5 | 5 | 4 | 5 |
| 63 | 63 | 5 | 5 | 5 | 5 | 5 | 4 | 4 | 5 |
| 64 | 63 | 5 | 5 | 5 | 5 | 4 | 5 | 4 | 5 |
| 65 | 125 | 5 | 5 | 5 | 5 | 5 | 4 | 5 | 5 |
| 66 | 125 | 4 | 5 | 5 | 5 | 5 | 5 | 4 | 5 |
| 67 | 125 | 5 | 5 | 4 | 5 | 4 | 5 | 5 | 5 |
| 68 | 125 | 5 | 5 | 5 | 5 | 5 | 5 | 5 | 5 |
| 69 | 125 | 5 | 5 | 5 | 5 | 5 | 5 | 5 | 5 |
| 70 | 250 | 5 | 5 | 3 | 5 | 3 | 5 | 4 | 5 |
| 71 | 250 | 4 | 5 | 4 | 5 | 3 | 5 | 3 | 5 |
| 72 | 250 | 5 | 5 | 5 | 5 | 4 | 5 | 4 | 5 |
| 73 | 250 | 5 | 5 | 5 | 5 | 3 | 3 | 4 | 5 |

Test Example 3

Herbicidal activity and phytotoxicity with pre-emergence treatment

For the test compounds, herbicidal activity against test weeds and phytotoxocity against wheat were determined according to the same procedure as Test Example 1 except that the applied amount of the solution of Formulation Example 1 is varied. The results are given in the following Table 10.

TABLE 10

| Comp. No. | Applied amount (g/ha) | Crops Whe | Weeds | | | | |
|---|---|---|---|---|---|---|---|
| | | | Sol | Abu | Xan | Pan | Ech |
| 5 | 125 | 0 | 5 | 5 | 5 | 5 | 5 |
| | 32 | 0 | 5 | 3 | 5 | 4 | 4 |
| 9 | 125 | 0 | 5 | 5 | 5 | 5 | 5 |
| | 32 | 0 | 5 | 3 | 5 | 4 | 3 |
| 12 | 125 | 0 | 5 | 5 | 5 | 5 | 4 |
| | 32 | 0 | 5 | 4 | 5 | 5 | 3 |
| 24 | 63 | 0 | 5 | 4 | 5 | 5 | 5 |
| | 16 | 0 | 5 | 2 | 5 | 4 | 4 |
| 26 | 63 | 0 | 5 | 4 | 5 | 5 | 5 |
| | 16 | 0 | 5 | 3 | 5 | 4 | 4 |
| 35 | 125 | 0 | 5 | 5 | 5 | 5 | 5 |
| | 32 | 0 | 4 | 2 | 5 | 4 | 4 |
| 47 | 125 | 0 | 5 | 5 | 5 | 5 | 5 |
| | 32 | 0 | 5 | 3 | 5 | 4 | 4 |
| 49 | 125 | 0 | 5 | 5 | 5 | 5 | 5 |
| | 32 | 0 | 5 | 3 | 5 | 4 | 3 |
| 50 | 125 | 0 | 5 | 5 | 5 | 5 | 5 |
| | 32 | 0 | 5 | 3 | 5 | 5 | 4 |
| 52 | 125 | 0 | 5 | 4 | 5 | 5 | 5 |
| | 32 | 0 | 5 | 2 | 5 | 4 | 4 |
| 53 | 125 | 0 | 5 | 4 | 5 | 5 | 5 |
| | 32 | 0 | 5 | 3 | 5 | 4 | 4 |
| 55 | 125 | 0 | 5 | 5 | 5 | 5 | 5 |
| | 32 | 0 | 4 | 2 | 5 | 4 | 3 |

The same procedure as Test Example 1 except that the solution of Formulation Example 2 is used and the applied amount is varied was conducted to evaluate the herbicidal activity and phytotoxicity against cotton of the test compounds. The evaluated results are given in the following Table 11. In this experiment, methyl ester compound (A) and phenoxyethyl ester compound (B) of 6-methoxy-2-(4,6-dimethoxypyrimidin-2-yl)oxybenzoic acid were synthesized according to the known method (Europena Patent Publication No. 321,846) and used as the comparative compounds.

TABLE 11

| Comp. No. | Applied amount (g/ha) | Crops Cot | Broad leaf weeds | | | | Narrow leaf weeds | | | |
|---|---|---|---|---|---|---|---|---|---|---|
| | | | Cal | Sol | Abu | Ama | Dig | Pan | Ech | Sor |
| 58 | 16 | 0 | 5 | 5 | 5 | 5 | 5 | 5 | 5 | 5 |
|  | 8 | 0 | 4 | 5 | 5 | 5 | 4 | 4 | 4 | 5 |
| 60 | 16 | 0 | 5 | 5 | 5 | 5 | 5 | 5 | 5 | 5 |
|  | 8 | 0 | 5 | 5 | 4 | 4 | 4 | 3 | 4 | 5 |
| A | 16 | 0 | 0 | 0 | 0 | 0 | 0 | 0 | 0 | 0 |
| B | 125 | 2 | 0 | 3 | 3 | 2 | 1 | 1 | 1 | 2 |
|  | 16 | 0 | 0 | 0 | 0 | 0 | 0 | 0 | 0 | 0 |

[Note]
Comparative compound A:

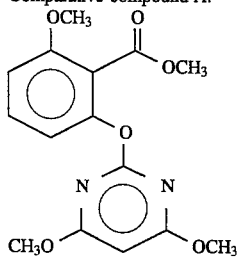

Comparative compound B:

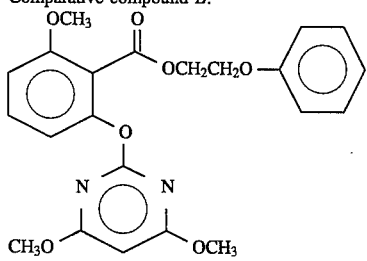

Test Example 4

Herbicidal activity and phytotoxicity with post-emergence treatment

For the test compounds, herbicidal activity against test weeds and phytotoxocity against wheat of the test compounds were determined according to the same procedure as Test Example 2 except that the applied amount of the solution of Formulation Example 1 is varied. The results are given in the following Table 12.

TABLE 12

| Comp. No. | Applied amount (g/ha) | Crops Whe | Weeds | | | | |
|---|---|---|---|---|---|---|---|
| | | | Sol | Abu | Xan | Pan | Ech |
| 3 | 63 | 0 | 5 | 5 | 5 | 5 | 5 |
|  | 16 | 0 | 5 | 4 | 4 | 4 | 4 |
| 9 | 63 | 0 | 5 | 5 | 5 | 5 | 5 |
|  | 32 | 0 | 5 | 4 | 5 | 5 | 5 |
| 11 | 63 | 0 | 5 | 5 | 5 | 5 | 5 |
|  | 16 | 0 | 5 | 3 | 5 | 5 | 4 |
| 26 | 63 | 0 | 5 | 4 | 5 | 5 | 5 |
|  | 16 | 0 | 5 | 3 | 5 | 4 | 5 |
| 30 | 63 | 0 | 5 | 5 | 5 | 5 | 5 |
|  | 16 | 0 | 5 | 4 | 5 | 5 | 4 |
| 35 | 125 | 0 | 5 | 5 | 5 | 5 | 5 |
|  | 32 | 0 | 5 | 4 | 5 | 5 | 4 |
| 47 | 125 | 0 | 5 | 5 | 5 | 5 | 5 |
|  | 32 | 0 | 5 | 3 | 5 | 4 | 4 |
| 48 | 125 | 0 | 5 | 5 | 5 | 5 | 5 |
|  | 32 | 0 | 5 | 3 | 5 | 5 | 5 |

TABLE 12-continued

| Comp. No. | Applied amount (g/ha) | Crops Whe | Weeds | | | | |
|---|---|---|---|---|---|---|---|
| | | | Sol | Abu | Xan | Pan | Ech |
| 49 | 125 | 0 | 5 | 5 | 5 | 5 | 5 |
|  | 32 | 0 | 5 | 3 | 5 | 5 | 4 |
| 50 | 125 | 0 | 5 | 4 | 5 | 5 | 5 |
|  | 32 | 0 | 5 | 2 | 5 | 4 | 5 |
| 56 | 125 | 0 | 5 | 5 | 5 | 5 | 5 |
|  | 32 | 0 | 5 | 3 | 5 | 5 | 4 |
| 57 | 125 | 0 | 5 | 5 | 5 | 5 | 5 |
|  | 32 | 0 | 4 | 3 | 5 | 5 | 4 |

The same procedure as Test Example 2 except that the solution of Formulation Example 2 is used and the applied amount is varied was conducted to evaluate the herbicidal activity and phytotoxicity against cotton of the test compounds. The evaluated results are given in the following Table 13. In this experiment, the same compounds (A) and (B) as in Test Example 3 above were used as the comparative compounds.

TABLE 13

| Comp. No. | Applied amount (g/ha) | Crops Cot | Broad leaf weeds Cal | Sol | Abu | Ama | Narrow leaf weeds Dig | Pan | Ech | Sor |
|---|---|---|---|---|---|---|---|---|---|---|
| 58 | 16 | 0 | 5 | 5 | 5 | 5 | 4 | 5 | 5 | 5 |
|  | 8 | 0 | 5 | 5 | 5 | 5 | 3 | 4 | 4 | 5 |
| 60 | 32 | 1 | 5 | 5 | 5 | 5 | 5 | 5 | 5 | 5 |
|  | 16 | 0 | 4 | 5 | 5 | 5 | 4 | 5 | 4 | 5 |
| A | 32 | 0 | 0 | 0 | 1 | 0 | 0 | 0 | 0 | 1 |
| B | 125 | 0 | 0 | 0 | 0 | 0 | 0 | 0 | 0 | 0 |
|  | 16 | 0 | 0 | 0 | 0 | 0 | 0 | 0 | 0 | 0 |

Test Example 5

Herbicidal activity and phytotoxicity with pre-emergence soil treatment (paddy field condition)

Squarish pots (30×15×10 cm) were filled with sterilized paddy field soil (piedmont clay, pH 5.5–6.0) and then the seeds of paddy weeds and rice plant were sown in the pot having the surface area of 450 cm$^2$. After the pot is submerged with water in the depth of 4 cm for one day, the predetermined amount of the solution of Formulation Example 3 which corresponds to the applied amount of 32 g, 63 g, 125 g or 250 g of the active ingredient per hectare was uniformly applied dropwise to the soil surface. The test plants were observed for 4 weeks after the treatment with the test compounds and then the herbicidal activity and the phytotoxicity against rice plant of the test compounds were evaluated on the basis of the evaluation standard as described in Table 5 above. The results are given in the following Table 14.

TABLE 14

| Comp. No. | Applied amount (g/ha) | Crops T-Ric | D-Ric | Weeds Ecg | Sag | Ele | Sap |
|---|---|---|---|---|---|---|---|
| 1 | 125 | 0 | 1 | 5 | 5 | 5 | 5 |
|  | 32 | 0 | 0 | 2 | 5 | 5 | 5 |
| 2 | 250 | 0 | 2 | 5 | 5 | 5 | 5 |
|  | 63 | 0 | 0 | 0 | 5 | 5 | 5 |
| 5 | 125 | 1 | 2 | 4 | 5 | 5 | 5 |
|  | 32 | 0 | 0 | 0 | 5 | 5 | 5 |
| 6 | 125 | 0 | 1 | 5 | 5 | 5 | 5 |
|  | 32 | 0 | 0 | 2 | 5 | 5 | 4 |
| 7 | 125 | 0 | 2 | 4 | 5 | 5 | 5 |
|  | 32 | 0 | 0 | 2 | 5 | 5 | 5 |
| 9 | 125 | 1 | 3 | 4 | 5 | 5 | 5 |
|  | 32 | 0 | 0 | 1 | 5 | 5 | 4 |
| 11 | 125 | 1 | 2 | 4 | 5 | 5 | 5 |
|  | 32 | 0 | 0 | 2 | 5 | 5 | 5 |
| 12 | 125 | 1 | 3 | 5 | 5 | 5 | 5 |
|  | 32 | 0 | 0 | 0 | 5 | 5 | 4 |
| 16 | 125 | 1 | 2 | 4 | 5 | 5 | 5 |
|  | 32 | 0 | 0 | 1 | 5 | 5 | 4 |
| 24 | 125 | 1 | 2 | 5 | 5 | 5 | 5 |
|  | 32 | 0 | 0 | 2 | 5 | 5 | 5 |
| 28 | 125 | 0 | 1 | 3 | 5 | 5 | 5 |
|  | 32 | 0 | 0 | 2 | 5 | 5 | 5 |
| 35 | 125 | 0 | 2 | 5 | 5 | 5 | 5 |
|  | 32 | 0 | 0 | 3 | 5 | 5 | 5 |
| 45 | 125 | 0 | 2 | 5 | 5 | 5 | 5 |
|  | 32 | 0 | 0 | 2 | 5 | 5 | 4 |
| 46 | 125 | 0 | 2 | 5 | 5 | 5 | 5 |
|  | 32 | 0 | 0 | 2 | 5 | 5 | 4 |
| 47 | 125 | 1 | 3 | 5 | 5 | 5 | 5 |
|  | 32 | 0 | 0 | 3 | 5 | 5 | 5 |
| 48 | 125 | 0 | 3 | 5 | 5 | 5 | 5 |
|  | 32 | 0 | 0 | 2 | 5 | 5 | 4 |
| 49 | 125 | 0 | 1 | 5 | 5 | 5 | 5 |
|  | 32 | 0 | 0 | 3 | 5 | 5 | 5 |
| 50 | 125 | 0 | 2 | 5 | 5 | 5 | 5 |
|  | 32 | 0 | 0 | 2 | 5 | 5 | 4 |
| 51 | 125 | 1 | 3 | 5 | 5 | 5 | 5 |
|  | 32 | 0 | 0 | 2 | 5 | 5 | 5 |
| 52 | 125 | 1 | 3 | 5 | 5 | 5 | 5 |
|  | 32 | 0 | 0 | 0 | 5 | 5 | 4 |
| 53 | 125 | 0 | 2 | 5 | 5 | 5 | 5 |
|  | 32 | 0 | 0 | 2 | 5 | 5 | 5 |
| 54 | 125 | 0 | 1 | 4 | 5 | 5 | 5 |
|  | 32 | 0 | 0 | 2 | 5 | 5 | 5 |
| 55 | 125 | 0 | 1 | 3 | 5 | 5 | 5 |
|  | 32 | 0 | 0 | 2 | 5 | 5 | 5 |
| 56 | 125 | 0 | 2 | 5 | 5 | 5 | 5 |
|  | 32 | 0 | 0 | 2 | 5 | 5 | 5 |
| 57 | 125 | 0 | 2 | 4 | 5 | 5 | 5 |
|  | 32 | 0 | 0 | 1 | 5 | 5 | 4 |

[Note]
T-Ric: Transplanted rice plant
D-Ric: Direct sowing rice plant

Test Example 6

Herbicidal activity and phytotoxicity with post-emergence foliage treatment (paddy field condition)

Squarish pots (30×15×10 cm) were filled with sterilized paddy field soil (piedmont clay, pH 5.5–6.0) and then the seeds of paddy weeds and rice plant were sown in the pot having the surface area of 450 cm$^2$ and then covered with soil of a thickness of 0.5 cm. The test plants were cultivated for 12 to 14 days in greenhouse of 20° to 25° C. When the test plants grew to the 2 to 3-leaves stage, they were treated by uniformly spraying the predetermined amount of the solution of Formulation Example 3, which corresponds to the applied amount of 16 g, 32 g, 63 g, 125 g or 250 g of the active ingredient per hectare, to the foliage part of the plants. The test paints were observed for 30 days after spray treatment to determine the herbicidal activity and phytotoxicity of the test compounds. The results were evaluated on the basis of the standard as described in Table 5 above and are given in the following Table 15.

TABLE 15

| Comp. No. | Applied amount (g/ha) | D-Ric | Ecg | Ech | Alo | Aes | Dig | Set |
|---|---|---|---|---|---|---|---|---|
| 1 | 63 | 0 | 5 | 5 | 5 | 5 | 5 | 5 |
|  | 32 | 0 | 5 | 4 | 5 | 5 | 5 | 4 |

TABLE 15-continued

| Comp. No. | Applied amount (g/ha) | D-Ric | Ecg | Ech | Alo | Aes | Dig | Set |
|---|---|---|---|---|---|---|---|---|
| 4 | 250 | 0 | 5 | 5 | 5 | 5 | 5 | 5 |
|   | 63 | 0 | 5 | 5 | 4 | 5 | 5 | 5 |
| 5 | 250 | 1 | 5 | 5 | 5 | 5 | 5 | 5 |
|   | 63 | 0 | 5 | 5 | 5 | 5 | 5 | 5 |
| 7 | 125 | 0 | 5 | 5 | 5 | 5 | 5 | 5 |
|   | 63 | 0 | 5 | 5 | 5 | 5 | 5 | 5 |
| 9 | 125 | 0 | 5 | 5 | 5 | 5 | 5 | 5 |
|   | 32 | 0 | 5 | 5 | 5 | 5 | 4 | 5 |
| 11 | 125 | 1 | 5 | 5 | 5 | 5 | 5 | 5 |
|   | 32 | 0 | 5 | 5 | 5 | 5 | 4 | 5 |
| 12 | 250 | 0 | 5 | 5 | 5 | 5 | 5 | 5 |
|   | 63 | 0 | 5 | 5 | 5 | 5 | 5 | 5 |
| 14 | 250 | 0 | 5 | 5 | 5 | 5 | 5 | 5 |
|   | 63 | 0 | 5 | 5 | 4 | 5 | 4 | 5 |
| 15 | 63 | 0 | 5 | 5 | 5 | 5 | 5 | 5 |
|   | 32 | 0 | 5 | 4 | 5 | 5 | 4 | 5 |
| 16 | 125 | 0 | 5 | 5 | 5 | 5 | 5 | 5 |
|   | 63 | 0 | 5 | 5 | 5 | 5 | 5 | 5 |
| 20 | 63 | 0 | 5 | 5 | 5 | 5 | 5 | 5 |
|   | 32 | 0 | 5 | 5 | 5 | 5 | 5 | 5 |
| 22 | 125 | 1 | 5 | 5 | 5 | 5 | 5 | 5 |
|   | 32 | 0 | 5 | 5 | 5 | 5 | 5 | 5 |
| 24 | 125 | 0 | 5 | 5 | 5 | 5 | 5 | 5 |
|   | 63 | 0 | 5 | 5 | 5 | 5 | 5 | 5 |
| 28 | 250 | 0 | 5 | 5 | 5 | 5 | 5 | 5 |
|   | 32 | 0 | 5 | 5 | 5 | 5 | 5 | 5 |
| 30 | 63 | 0 | 5 | 5 | 5 | 5 | 5 | 5 |
|   | 16 | 0 | 5 | 5 | 5 | 5 | 3 | 5 |
| 32 | 125 | 0 | 5 | 5 | 5 | 5 | 5 | 5 |
|   | 32 | 0 | 5 | 5 | 5 | 5 | 5 | 4 |
| 33 | 125 | 1 | 5 | 5 | 5 | 5 | 5 | 5 |
|   | 32 | 0 | 5 | 4 | 5 | 5 | 4 | 5 |
| 35 | 125 | 0 | 5 | 5 | 5 | 5 | 5 | 5 |
|   | 32 | 0 | 5 | 5 | 5 | 5 | 4 | 5 |
| 36 | 125 | 0 | 5 | 5 | 5 | 5 | 5 | 5 |
|   | 63 | 0 | 5 | 5 | 5 | 5 | 5 | 5 |
| 38 | 125 | 0 | 5 | 5 | 5 | 5 | 5 | 5 |
|   | 32 | 0 | 5 | 5 | 4 | 5 | 5 | 5 |
| 39 | 250 | 0 | 5 | 5 | 5 | 5 | 5 | 5 |
|   | 63 | 0 | 5 | 5 | 5 | 5 | 5 | 4 |
| 40 | 125 | 0 | 5 | 5 | 5 | 5 | 5 | 5 |
|   | 32 | 0 | 5 | 4 | 5 | 5 | 4 | 4 |
| 41 | 250 | 0 | 5 | 5 | 5 | 5 | 5 | 5 |
|   | 63 | 0 | 5 | 5 | 4 | 5 | 5 | 5 |
| 42 | 125 | 0 | 5 | 5 | 5 | 5 | 5 | 5 |
|   | 32 | 0 | 5 | 5 | 5 | 5 | 5 | 5 |
| 44 | 125 | 0 | 5 | 5 | 5 | 5 | 5 | 5 |
|   | 63 | 0 | 5 | 5 | 4 | 5 | 5 | 5 |
| 47 | 250 | 0 | 5 | 5 | 5 | 5 | 5 | 5 |
|   | 63 | 0 | 5 | 5 | 5 | 5 | 5 | 5 |
| 48 | 250 | 1 | 5 | 5 | 5 | 5 | 5 | 5 |
|   | 63 | 0 | 5 | 5 | 5 | 5 | 5 | 5 |
| 49 | 125 | 0 | 5 | 5 | 5 | 5 | 5 | 5 |
|   | 63 | 0 | 5 | 5 | 5 | 5 | 5 | 5 |
| 50 | 125 | 0 | 5 | 5 | 5 | 5 | 5 | 5 |
|   | 32 | 0 | 5 | 5 | 5 | 5 | 4 | 5 |
| 52 | 125 | 0 | 5 | 5 | 5 | 5 | 5 | 5 |
|   | 32 | 0 | 5 | 5 | 5 | 5 | 4 | 5 |
| 53 | 250 | 0 | 5 | 5 | 5 | 5 | 5 | 5 |
|   | 32 | 0 | 5 | 5 | 5 | 5 | 3 | 5 |
| 54 | 250 | 0 | 5 | 5 | 5 | 5 | 5 | 5 |
|   | 63 | 0 | 5 | 5 | 5 | 5 | 5 | 5 |
| 55 | 250 | 0 | 5 | 5 | 5 | 5 | 5 | 5 |
|   | 32 | 0 | 5 | 5 | 5 | 5 | 4 | 5 |
| 56 | 125 | 0 | 5 | 5 | 5 | 5 | 5 | 5 |
|   | 63 | 0 | 5 | 5 | 5 | 5 | 5 | 5 |
| 57 | 63 | 0 | 5 | 5 | 5 | 5 | 5 | 5 |

Test Example 7

Herbicidal activity and phytotoxicity with post-emergence foliage treatment (early foliage stage treatment: one-leaf stage).

The comparative compound C as disclosed in European Patent Publication No. 321,648 was synthesized according to the procedure described in said patent and was compared with the compound of the present invention. According to the procedure as Test Example 6, the seeds of rice plant and weeds were sown, cultivated at 20° to 25° C. for 7 days and then treated by uniformly spraying the solution of Formulation Example 3 to the foliage part of the plants. The test plants were observed for 20 days after treatment of the test compounds and then their herbicidal activity against test weeds and phytotoxocity against rice plant were determined. The results are given in the following Table 16.

TABLE 16

Comparative compound C:

$$\text{structure: central benzene ring with two ortho -O- linkages to 4,6-dimethoxypyrimidin-2-yl groups, and a -C(=O)-O-N=C(CH_3)_2 oxime ester group}$$

| Comp. No. | Applied amount (g/ha) | D-Ric | Ecg | Ech | Alo | Aes | Dig | Set |
|---|---|---|---|---|---|---|---|---|
| C | 500 | 5 | — | — | — | — | — | — |
|   | 250 | 4 | — | — | — | — | — | — |
|   | 63 | 1 | 5 | 5 | 5 | 5 | 5 | 5 |
|   | 32 | 0 | 5 | 5 | 4 | 5 | 5 | 5 |
| 4 | 1000 | 1 | — | — | — | — | — | — |
|   | 500 | 0 | — | — | — | — | — | — |
|   | 125 | 0 | 5 | 5 | 5 | 5 | 5 | 5 |
|   | 63 | 0 | 5 | 5 | 5 | 5 | 5 | 5 |
| 12 | 500 | 0 | — | — | — | — | — | — |
|   | 250 | 0 | — | — | — | — | — | — |
|   | 63 | 0 | 5 | 5 | 4 | 5 | 5 | 5 |
|   | 32 | 0 | 5 | 5 | 3 | 5 | 5 | 4 |
| 28 | 500 | 0 | — | — | — | — | — | — |
|   | 250 | 0 | — | — | — | — | — | — |
|   | 63 | 0 | 5 | 5 | 5 | 5 | 5 | 5 |
|   | 32 | 0 | 5 | 5 | 4 | 5 | 5 | 3 |
| 35 | 500 | 1 | — | — | — | — | — | — |
|   | 250 | 0 | — | — | — | — | — | — |
|   | 63 | 0 | 5 | 5 | 5 | 5 | 5 | 5 |
|   | 32 | 0 | 5 | 5 | 4 | 5 | 5 | 4 |
| 49 | 500 | 2 | — | — | — | — | — | — |
|   | 250 | 1 | — | — | — | — | — | — |
|   | 63 | 0 | 5 | 5 | 5 | 5 | 5 | 5 |
|   | 32 | 0 | 5 | 5 | 5 | 5 | 5 | 5 |
| 53 | 500 | 2 | — | — | — | — | — | — |
|   | 250 | 0 | — | — | — | — | — | — |
|   | 63 | 0 | 5 | 5 | 4 | 5 | 5 | 5 |
|   | 32 | 0 | 5 | 5 | 3 | 5 | 5 | 4 |
| 55 | 500 | 1 | — | — | — | — | — | — |
|   | 250 | 0 | — | — | — | — | — | — |
|   | 63 | 0 | 5 | 5 | 5 | 5 | 5 | 5 |
|   | 32 | 0 | 5 | 5 | 4 | 5 | 5 | 3 |

Test Example 8

Herbicidal activity and phytotoxicity with post-emergence foliage treatment (early stage foliage treatment:two-leaves stage)

The same comparative compound C as Test Example 7 was compared with the test compounds of the present invention. According to the same procedure as Test Example 6, the seeds of rice plant and weeds were sown, cultivated at 20° to 25° C. for 11 days and then treated by uniformly spraying the solution of Formulation Example 3 to the foliage part of the plants. The test plants were observed for 20 days after treatment of the test compounds and then their herbicidal activity against test weeds and phytotoxocity against rice plant were determined. The results are given in the following Table 17.

TABLE 17

| Comp. No. | Applied amount (g/ha) | D-Ric | Ecg | Ech | Alo | Aes | Dig | Set |
|---|---|---|---|---|---|---|---|---|
| C | 1000 | 4 | — | — | — | — | — | — |
|   | 500 | 3 | — | — | — | — | — | — |
|   | 125 | 1 | 5 | 5 | 5 | 5 | 5 | 5 |
|   | 63 | 0 | 5 | 5 | 3 | 5 | 3 | 4 |
| 12 | 1000 | 1 | — | — | — | — | — | — |
|   | 500 | 0 | — | — | — | — | — | — |
|   | 125 | 0 | 5 | 5 | 5 | 5 | 5 | 5 |
|   | 63 | 0 | 5 | 5 | 3 | 5 | 4 | 4 |
| 28 | 1000 | 2 | — | — | — | — | — | — |
|   | 500 | 1 | — | — | — | — | — | — |
|   | 125 | 0 | 5 | 5 | 5 | 5 | 5 | 5 |
|   | 63 | 0 | 5 | 5 | 5 | 5 | 5 | 5 |
| 35 | 1000 | 2 | — | — | — | — | — | — |
|   | 500 | 1 | — | — | — | — | — | — |
|   | 125 | 0 | 5 | 5 | 5 | 5 | 5 | 5 |
|   | 63 | 0 | 5 | 5 | 5 | 5 | 5 | 5 |
| 42 | 1000 | 2 | — | — | — | — | — | — |
|   | 500 | 1 | — | — | — | — | — | — |
|   | 125 | 0 | 5 | 5 | 5 | 5 | 5 | 5 |
|   | 63 | 0 | 5 | 5 | 5 | 5 | 5 | 5 |
| 49 | 1000 | 2 | — | — | — | — | — | — |
|   | 500 | 1 | — | — | — | — | — | — |
|   | 125 | 0 | 5 | 5 | 5 | 5 | 5 | 5 |
|   | 63 | 0 | 5 | 5 | 3 | 5 | 4 | 4 |
| 50 | 1000 | 2 | — | — | — | — | — | — |
|   | 500 | 1 | — | — | — | — | — | — |
|   | 125 | 0 | 5 | 5 | 5 | 5 | 5 | 5 |
|   | 63 | 0 | 5 | 5 | 5 | 5 | 5 | 5 |
| 53 | 1000 | 2 | — | — | — | — | — | — |
|   | 500 | 1 | — | — | — | — | — | — |
|   | 125 | 0 | 5 | 5 | 5 | 5 | 5 | 5 |
|   | 63 | 0 | 5 | 5 | 5 | 5 | 5 | 5 |
| 55 | 1000 | 2 | — | — | — | — | — | — |
|   | 500 | 1 | — | — | — | — | — | — |
|   | 125 | 0 | 5 | 5 | 5 | 5 | 5 | 5 |
|   | 63 | 0 | 5 | 5 | 5 | 5 | 5 | 5 |

As can be seen from the results of Test Example 6 and 7, the compound of the present invention has an excellent herbicidal activity against both of narrow leaf weeds and broad leaf weeds, including barnyardgrass, and also has a superior safety against useful crops. In addition, it can also be noted that the safety of the compound according to the present invention against direct sowing rice plant is two times or more as high as that of the known compound C.

Although this invention has been described in its preferred form with a certain degree of particularity, it is appreciated by those skilled in the art that the present disclosure of the preferred form has been made only by way of example and that numerous changes in the details of the construction, combination and arrangement of parts may be resorted to without departing from the spirit and scope of the invention.

What is claimed is:

1. A pyrimidine derivative represented by the following formula (I):

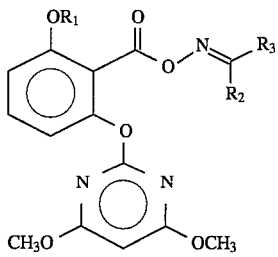

in which $R_1$ represents 4,6-dimethoxy-2-pyrimidinyl, $C_1$–$C_4$ alkyl, $C_2$–$C_4$ alkenyl, acetyl, $C_1$–$C_4$ alkylsulfonyl, thienylmethyl or furylmethyl;

$R_2$ represents hydrogen, halogen, cyano, nitro, $C_1$–$C_8$ alkyl, $C_1$–$C_8$ alkoxy, $C_1$–$C_8$ alkylthio, $C_1$–$C_8$ alkoxycarbonyl, $C_2$–$C_4$ alkenyloxycarbonyl, $C_2$–$C_8$ alykenyl, phenylmethoxycarbonyl, mono- or di-$C_1$–$C_4$ alkylaminocarbonyl, phenyl-$C_1$–$C_4$ alkylaminocarbonyl wherein the phenyl moiety can be optionally substituted with halogen, $C_1$–$C_2$ alkyl or $C_1$–$C_2$ alkoxy, furylmethylaminocarbonyl, phenyl, $C_3$–$C_6$ cycloalkyl, benzyl, phenoxy, phenylthio, $C_2$–$C_8$ alkenyl, $C_3$–$C_6$ cycloalkyl, benzyl, or $C_1$–$C_8$ alkylcarbonyl; and $R_3$ represents a phenyl group which can be optionally substituted with substituent selected from the group consisting of halogen, cyano, nitro, $C_1$–$C_4$ alkyl, $C_3$–$C_6$ cycloalkyl, $C_1$–$C_4$ alkoxy, $C_2$–$C_4$ alkenyloxy, $C_1$–$C_4$ alkylthio, $C_1$–$C_4$ alkylamino, phenyl, phenoxy, benzyloxy, acetoxy, $C_1$–$C_4$ acyl, $C_1$–$C_4$ acyloxy, or $C_2$–$C_4$ alkenyl, or represents a group of formula —$COR_4$ wherein $R_4$ represents hydrogen, $C_1$–$C_4$ alkyl, $C_2$–$C_4$ alkenyl, $C_3$–$C_6$ cycloalkyl, benzyl, phenyl, $C_1$–$C_4$ alkoxy, $C_2$–$C_4$ alkenyloxy, $C_3$–$C_6$ cycloalkyloxy, benzyloxy, phenoxy, $C_1$–$C_4$ alkylthio, $C_2$–$C_4$ alkenylthio, $C_3$–$C_6$ cycloalkylthio, benzylthio, phenylthio, $C_1$–$C_4$ alkylamino, phenylamino, benzylamino.

2. The pyrimidine derivative of formula (I) according to claim 1, characterized in that $R_1$ represents 4,6-dimethoxy-2-pyrimidinyl;

$R_2$ represents hydrogen, halogen, cyano, $C_1$–$C_8$ alkyl, $C_1$–$C_4$ alkoxy, $C_1$–$C_4$ alkylthio, $C_1$–$C_4$ alkoxycarbonyl, mono- or di-$C_1$–$C_4$ alkylaminocarbonyl, phenyl-$C_1$–$C_2$ alkylaminocarbonyl wherein the phenyl moiety is optionally substituted with halogen, $C_1$–$C_2$ alkyl or $C_1$–$C_2$ alkoxy, furylmethylaminocarbonyl or phenyl; and $R_3$ represents a phenyl group which is unsubstituted or substituted with halogen, cyano, nitro, $C_1$–$C_4$ alkyl, $C_1$–$C_4$ alkoxy, allyloxy, $C_1$–$C_4$ alkylthio, $C_1$–$C_4$ alkylamino, phenoxy, benzyloxy or acetoxy, or represents a group of formula -$COR_4$ wherein $R_4$ represents $C_1$–$C_4$ alkoxy, $C_1$–$C_4$ alkyl, benzyloxy or benzylamino.

3. The pyrimidine derivative of formula (I) according to claim 2, characterized in that $R_1$ represents 4,6-dimethoxy-2-pyrimidinyl;

$R_2$ represents hydrogen, chloro, cyanophenyl, $C_1$–$C_8$ alkyl, methoxy, methylthio, $C_1$–$C_2$ alkoxycarbonyl, propylaminocarbonyl, dimethylaminocarbonyl, benzylaminocarbonyl wherein the benzyl moiety is optionally substituted with chloro, methyl or methoxy, 2'-phenylethylaminocarbonyl, furylmethylaminocarbonyl or phenyl; and $R_3$ represents phenyl group which is unsubstituted or substituted with a substituent selected from the group consisting of chloro, fluoro, cyano, nitro, methyl, methoxy, ethoxy, butoxy, allyloxy, methylthio, dimethylamino, phenoxy, benzyloxy or acetoxy or represents a group of formula -$COR_4$ wherein $R_4$ represents methoxy, ethoxy, methyl, benzyloxy or benzylamino.

4. The pyrimidine derivative of formula (I) according to claim 1, characterized in that $R_1$ represents $C_1$–$C_2$ alkyl, $C_2$–$C_4$ alkenyl, allyl, acetyl, methylsulfonyl, thienylmethyl or furylmethyl;

$R_2$ represents hydrogen, $C_1$–$C_4$ alkyl, $C_1$–$C_4$ alkoxy, $C_1$–$C_4$ alkylthio, cyano or $C_1$–$C_4$ alkoxycarbonyl; and $R_3$ represents phenyl group which can be unsubstituted or substituted with $C_1$–$C_4$ alkyl, $C_1$–$C_4$ alkoxy or $C_2$–$C_4$ alkenyl.

5. The pyrimidine derivative of formula (I) according to claim 4, characterized in that $R_1$ represents methyl, ethyl, allyl, acetyl, methylsulfonyl, thienylmethyl or furylmethyl;

$R_2$ represents hydrogen, methyl, methylthio, cyano or methoxycarbonyl; and $R_3$ represents phenyl group which is unsubstituted or substituted with methyl or methoxy.

6. A pyridine thio ester compound represented by the following formula (II):

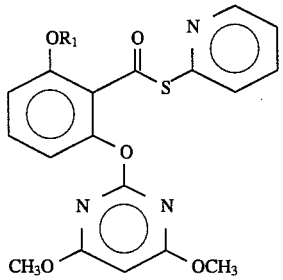

in which $R_1$ represents 4,6-dimethoxy-2-pyrimidinyl, $C_1$–$C_4$ alkyl, $C_2$–$C_4$ alkenyl, acetyl, alkylsulfonyl, thienylmethyl or furylmethyl.

7. A process for preparing a pyrimidine derivative represented by the following formula (I):

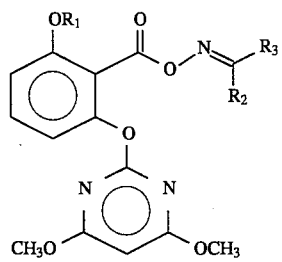

in which $R_1$ represents 4,6-dimethoxy-2-pyrimidinyl, $C_1$–$C_4$ alkyl, $C_2$–$C_4$ alkenyl, acetyl, $C_1$–$C_4$ alkylsulfonyl, thienylmethyl or furylmethyl;

$R_2$ represents hydrogen, halogen, cyano, nitro, $C_1$–$C_8$ alkyl, $C_1$–$C_8$ alkoxy, $C_1$–$C_8$ alkylthio, $C_1$–$C_8$ alkoxycarbonyl, $C_2$–$C_4$ alkenyloxycarbonyl, phenylmethoxycarbonyl, mono- or di-$C_1$–$C_4$ alkylaminocarbonyl, phenyl-$C_1$–$C_4$ alkylaminocarbonyl; wherein the phenyl moiety can be optionally substituted with halogen, $C_1$–$C_2$ alkyl or $C_1$–$C_2$ alkoxy; furylmethylaminocarbonyl, phenyl, $C_2$–$C_8$ alkenyl, $C_3$–$C_6$ cycloalkyl, benzyl, phenoxy, phenylthio or $C_1$–$C_8$ alkylcarbonyl; and $R_3$ represents a phenyl group which can be optionally substituted with substituent selected from the group consisting of halogen, cyano, nitro, $C_1$–$C_4$ alkyl, $C_3$–$C_6$ cycloalkyl, $C_1$–$C_4$ alkoxy, $C_2$–$C_4$ alkenyloxy, $C_1$–$C_4$ alkylthio, $C_1$–$C_4$ alkylamino, phenyl, phenoxy, benzyloxy, acetoxy, $C_1$–$C_4$ acyl, $C_1$–$C_4$ acyloxy, or $C_2$–$C_4$ alkenyl, or represents a group of formula -$COR_4$ wherein $R_4$ represents hydrogen, $C_1$–$C_4$ alkyl, $C_2$–$C_4$ alkenyl, $C_3$–$C_6$ cycloalkyl, benzyl, phenyl, $C_1$–$C_4$ alkoxy, $C_2$–$C_4$ alkenyloxy, $C_3$–$C_6$ cycloalkyloxy, benzyloxy, phenoxy, $C_1$–$C_4$ alkylthio, $C_2$–$C_4$ alkenylthio, $C_3$–$C_6$ cycloalkylthio, benzylthio, phenylthio, $C_1$–$C_4$ alkylamino, phenylamino, or benzylamino, characterized in that a compound represented by the following formula (II):

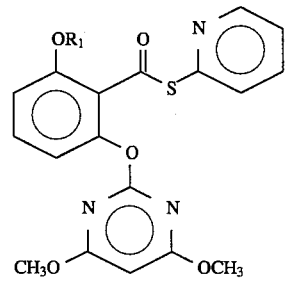

in which $R_1$ is defined as above, is reacted with a compound represented by the following formula (III):

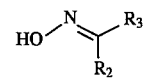

in which $R_2$ and $R_3$ are defined as above, in a solvent in the presence of a metal salt.

8. The process according to claim 7, characterized in that the metal salt is a cupric salt.

9. The process according to claim 8, characterized in that the metal salt is cupric chloride or cupric bromide.

10. The process according to claim 7, characterized in that the solvent is a halogenated hydrocarbon solvent or a nitrile.

11. A herbicidal composition comprising one or more of the pyrimidine derivative of formula (I) according to claim 1 as an active ingredient, together with a conventional agriculturally acceptable carrier.

12. The herbicidal composition according to claim 11 for controlling weeds grown in the field of cotton, rice plant or wheat.

13. The herbicidal composition according to claim 12 for controlling weeds grown in the field of direct sowing rice plant.

* * * * *